United States Patent [19]
Gordon-Wylie et al.

[11] Patent Number: 6,011,152
[45] Date of Patent: Jan. 4, 2000

[54] SYNTHESIS OF MACROCYCLIC TETRAAMIDO-N LIGANDS

[75] Inventors: Scott W. Gordon-Wylie; Terrence J. Collins, both of Pittsburgh, Pa.

[73] Assignee: Carnegie Mellon University, Pittsburgh, Pa.

[21] Appl. No.: 09/158,487

[22] Filed: Sep. 22, 1998

Related U.S. Application Data

[62] Division of application No. 08/681,187, Jul. 22, 1996.

[51] Int. Cl.$^7$ .................. C07D 257/02; C07D 255/02
[52] U.S. Cl. .................. 540/474; 540/465; 540/470; 562/565; 564/158; 564/305
[58] Field of Search .................. 540/450–453, 540/463, 465, 470, 474; 564/158, 305; 562/565

[56] References Cited

U.S. PATENT DOCUMENTS

| | | | |
|---|---|---|---|
| 4,517,122 | 5/1985 | Tomalia et al. | 260/239.3 |
| 4,577,042 | 3/1986 | Collins et al. | 564/158 |
| 4,758,682 | 7/1988 | Collins et al. | 556/137 |
| 5,189,160 | 2/1993 | Memeger, Jr. | 540/460 |
| 5,247,075 | 9/1993 | Parker et al. | 540/465 |
| 5,298,618 | 3/1994 | Speranza et al. | 540/454 |

OTHER PUBLICATIONS

Bradshaw et al., Aza–Crown Macrocycles, Chap X., pp. 555–556 John Wiley & Sons, Inc., 1993.

Thesis Of Workman, Carnegie–Mellon Univ., 1992.

A. Paul Krapcho, Edwin G. E. Jahngen, Jr., and David S. Kashdan, Route to Monesters of Malonic Acids, Tetrahedron Letters Nos. 32, pp. 2721–2723, 1994.

G. A. Fletcher and J. H. Jones, A List of Amino–Acid Derivatives Which Are Useful in Peptide Synthesis, Int. J. Peptide Protein Res. 4, 1972, 347–371, Jun. 10, 1972.

Jose M. Workman, Routes to Multimetallic High Oxidation State Transition Metal Complexes, Carnegie Mellon University, Mellon College of Science, Jul. 23, 1992.

Terrence J. Collins, Designing Ligands for Oxidizing Complexes, Department of Chemistry, Carnegie Mellon University, Accounts of Chemical Research, 1994, 27, p. 279.

Masaru Nakamura, Mitsuko Toda and Hiroko Saito, Fluorimetric Determination of Aromatuc Aldehydes With 4,5–Dimethoxyl–1,2–Diaminobenzene, Analytica Chimica Acta, 134 (1982) 39–45.

Erich Stuart Uffelman, Macrocyclic Tetraamido–N Ligands that Stabilize High Valent Complexes of Chromium, Maganese, Iron, Cobalt, Nickel and Copper, California Institute of Technology, Aug. 19, 1991.

Theodora W. Greene, Protective Groups in Organic Synthesis, Harvard University, John Wiley & Sons, 1981.

Kimberely K. Kostka, Synthesis and Characterization of High–Valent Iron Complexes of Macrocyclic Tetraamido–N Ligands, Carnegie Mellon University, Jul. 19, 1993.

Nathan L. Drake, Harry D. Anspon, et al. Synthetic Antimarlarials. Some Derivatives of 8–Aminoquinoline, Laboratories of the University of Maryland, vol. 68, p. 1536, Aug. 1946.

Richard J. Bushby and Michael D. Pollard, The Introduction of Alkylidene Substituents into the 4–Position of the 3,3,5,5–Tetramethyl–Δ–pyrazoline Nucleus by the Thioketone plus Diazoalkane Reaction: Synthesis of Tetrasubstituted Episulphides and Alkenes.

Bradshaw, et al., Chap. IV in Aza–Crown Macrocycles, Interscience Publication, Joh Wiley 1993, p. 146.

*Primary Examiner*—Mukund J. Shah
*Assistant Examiner*—Pavanaram K Sripada
*Attorney, Agent, or Firm*—Kirkpatrick & Lockhart LLP

[57] ABSTRACT

New synthetic methods for the preparation of macrocyclic amido-N donor ligands are provided. The primary method of the present invention involves in general only two synthetic steps. In the first step, an α or β amino carboxylic acid is allowed to react with an optimal (approximately stoichiometric) amount of an activated malonate or oxalate derivative with mild heating. Upon completion of the double coupling reaction, hydrolysis of the reaction mixture yields a diamide containing intermediate (a macro linker). In the second step, stoichiometric amounts of a diamine, preferably an orthophenylene diamine, are added to the macro linker intermediate in the presence of a coupling agent and heat. This second double coupling reaction, is allowed to proceed for a period of time sufficient to produce a macrocyclic tetraamido compound. The substituent groups on the α or β amino carboxylic acid, the malonate, and the aryl diamine may all be selectively varied so that the resulting tetraamido macrocycle can be tailored to specific desired end uses. The macrocyclic tetraamide ligand may then be complexed with a metal, such as a transition metal, and preferably the middle and later transition metals, to form a robust chelate complex suitable for catalyzing oxidation reactions.

28 Claims, 3 Drawing Sheets

SYNTHESIS OF MACROCYCLIC TETRAAMIDO-N LIGANDS

This application is a division of co-pending U.S. application Ser. No. 08/681,187 filed Jul. 22, 1996.

This invention was made in part with funding from the National Institute of Health, Contract No. GM-44867 and the National Science Foundation, Contract No. CHE9319505. The U.S. government may have rights in this invention.

BACKGROUND OF THE INVENTION

1. Field of the Invention

The invention relates to synthetic methods for producing macrocyclic compounds, and more particularly, to synthetic methods for producing tetraamido macrocyclic ligands and metal chelate complexes as pre catalysts for oxidation reactions.

2. Description of the Invention Background

Complexes of high oxidation state transition metals are known to function as oxidants in numerous biological reactions under the influence of a protein matrix and in recent years a widespread interest in understanding the mechanism of action and the reactivity of certain monooxygenase catalysts has developed. However, in the absence of a protein matrix to direct the oxidizing power towards a specific substrate, high oxidation state transition metal complexes tend to exhibit low oxidative selectivity and will instead oxidize any available substrate. Since the ligand complement is available in high local concentration as a possible substrate, oxidative degradation of the ligand complement has been a formidable impediment to obtaining long lived oxidation catalysts in the absence of a stabilizing matrix.

Collins, T. J., "Designing Ligands for Oxidizing Complexes," *Accounts of Chemical Research*, 279, Vol. 27, No. 9 (1994), describes a design oriented approach for obtaining ligands that are resistant to oxidative degradation when coordinated to highly oxidizing metal centers. Several diamido-N-diphenoxido and diamido-N-alkoxido acyclic chelate compounds and macrocyclic tetraamido-N chelate compounds are described in the Collins *Accounts of Chemical Research* article.

An azide based synthetic route to macrocyclic tetraamido ligands is described in Uffelman, E. S., Ph.D. Thesis, California Institute of Technology, (1992). Synthesis of the tetraamido ligands via the azide based route developed by Uffelman proceeds generally as follows:

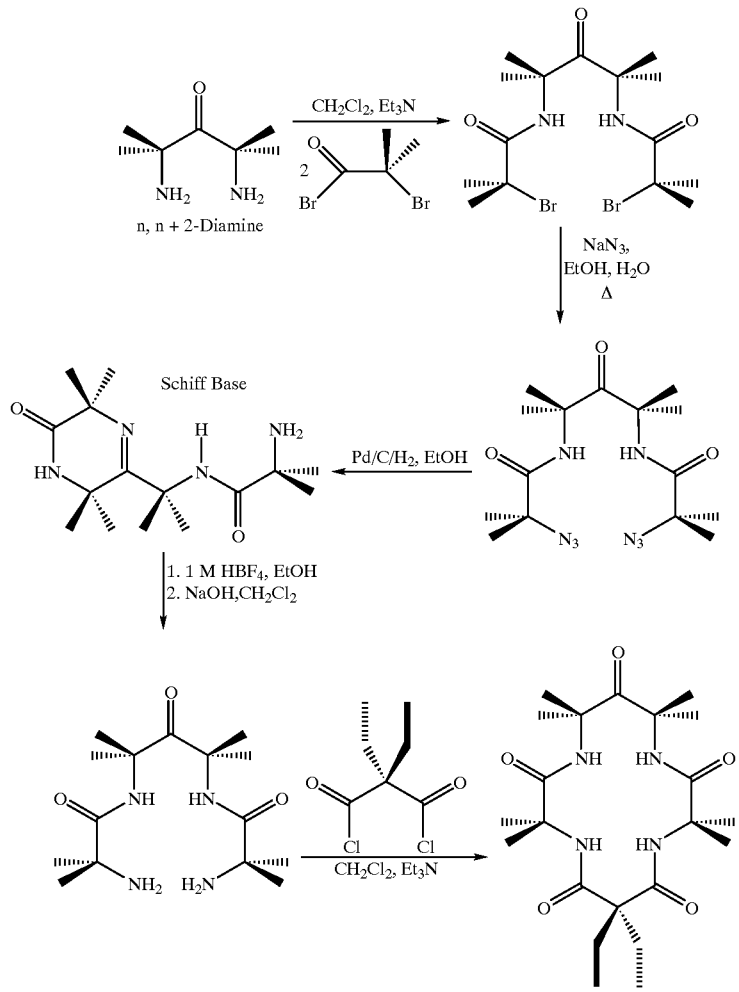

Synthesis of an aryl bridged tetraamido ligand via the azide based route proceeds as follows:

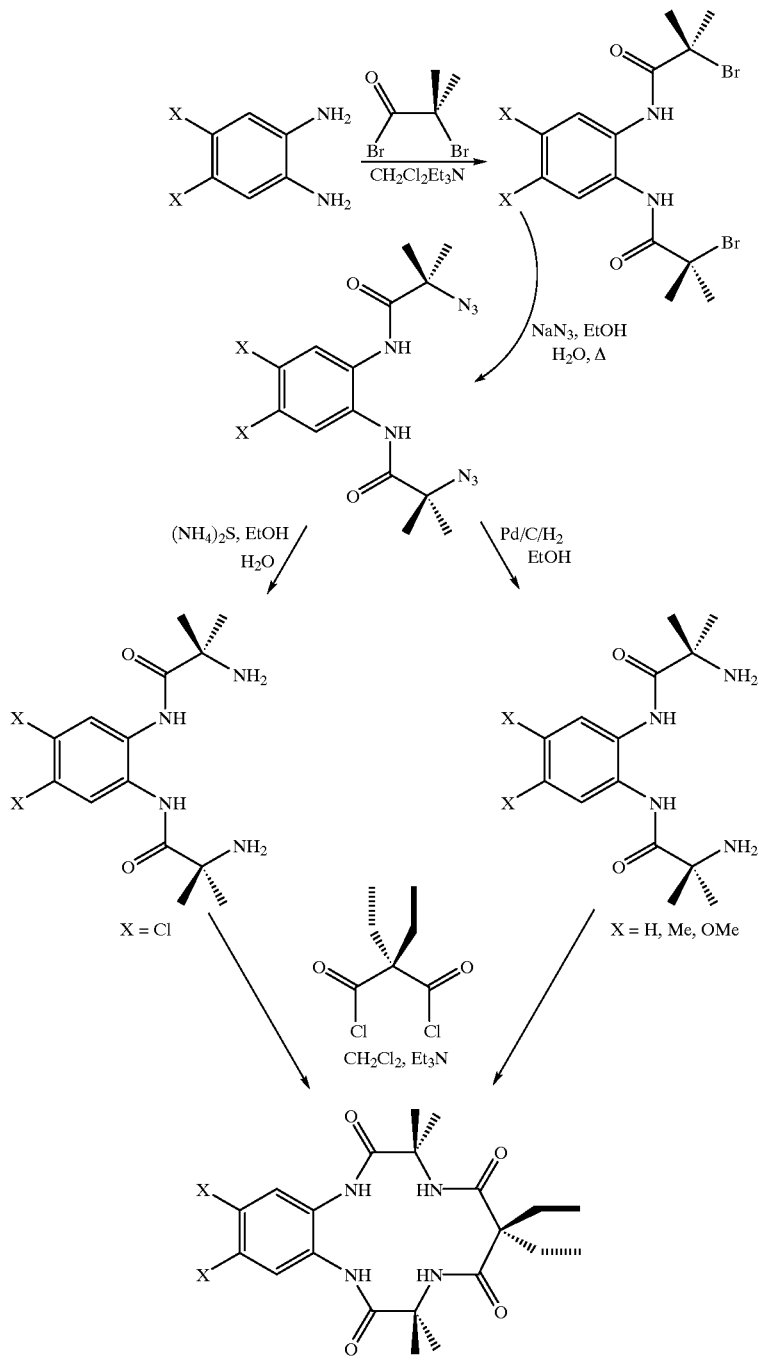

5,6: (4,5-Di-X-Benzo) -3,8,11,13-tetraoxo-2,2,9,9-tetramethyl-12,12-diethyl-1,4,7,10-tetraazacyclotridecane (or Tetramethyl diethyl di-X-benzene (TMDE-DXB, where X=Cl, H, Me, OMe))

The yield of the azide based method is about 25% for the final ring closing step but only about 5–10% for the combined sequence of steps starting from the diamine. This method generates new C—N bonds via formation of azide intermediates. The generation of the C—N bonds, however, is not very effective, at least as to yield. With each step of the process, the yield is reduced further so that the overall yield of the desired tetraamido ligand is comparatively low. Furthermore, the azide based method produces high energy intermediates.

There is a need for an alternative method of producing tetraamido ligands. There is also a need to improve the yield of such ligands. Finally, there is a need for a method of producing tetraamido ligands that are resistant to oxidative degradation and in which the various substituent groups can be controlled to tailor the ligands and the metallo complexes they form for specific end uses.

SUMMARY OF THE INVENTION

The foregoing needs are met by the method of the present invention and the compounds produced thereby. This method provides powerful new synthetic routes for the preparation of macrocyclic amido-N donor ligands, and particularly those with oxidatively robust substituents. The primary method of the present invention substantially increases the yield, and reduces the number of steps, as well as the time and the cost of the process as compared to the prior art azide method. Importantly, the new synthetic method reduces the hazards inherent to the azide method due to that method's high energy intermediates.

The method of the present invention includes in general two steps. In the first step, an amino carboxylic acid, preferably an α or β amino carboxylic acid, is dissolved in a supporting solvent and heated with an activated derivative selected from the group consisting of oxalates and malonates, such as a substituted malonyl dichloride in the presence of a base, to form an intermediate. The amino carboxylic acid is preferably in an amount that is approximately the stoichiometric amount, and most preferably in an amount somewhat greater than the stoichiometric amount. Any solvent suitable for performing acylations will suffice. However, if the solubility of the amino acid starting materials in organic solvents is limited, the preferred solvents are pyridine, dimethyl formamide (DMF) or any suitable aprotic solvent. Following completion of the selective double coupling reaction, typically 72–144 hrs when pyridine is used as the solvent/base, a diamide dicarboxyl-containing intermediate, sometimes referred to herein as a macro linker, is isolated. If acyl chlorides are employed in the synthesis of such macro linker intermediate, both the yields and ease of isolation of the intermediate can be improved by ensuring that the heat added in step 1 does not exceed 70° C. and that any reactive intermediates formed during the acylation reaction are carefully hydrolyzed prior to workup.

In the second step of the method of the present invention, a diamine is added to the intermediate in the presence of a solvent and a coupling agent. The resulting mixture is heated and the reaction is allowed to proceed for a period of time sufficient to produce macrocyclic tetraamido compounds via a selective double coupling reaction, typically 48–72 hours at reflux when pyridine is employed as the solvent. Longer ring closure times are necessary if substantial steric hindrance or hydrogen bonding substituents are present. Typically, stoichiometric amounts of an aryl or alkyl diamine, for example, an orthophenylene diamine, are used.

The preferred coupling agents are phosphorus halide compounds, such as $PBr_3$, $PCl_3$ or $POCl_3$, or pivaloyl chloride. The phosphorus halides are employed as powerful dehydrating agents for the condensation of amines and carboxylic acids to form amides. Pivaloyl chloride on the other hand is preferred for the preparation of mixed anhydride and oxazalone intermediates. Yields are improved if moisture is excluded during the second, ring closing step.

The substituent groups on the α or β amino carboxylic acid, the activated oxalate or malonate derivative, and the diamine may all be selectively varied so that the resulting tetraamido macrocycle can be tailored to specific desired end uses. This highly efficient streamlined synthesis not only tolerates a comparatively wide range of functional groups, but also employs relatively low cost reagents and is compatible with large scale operation, all of which are highly desirable synthetic features.

Variation of the substituents has little or no effect on the methodology. In varying the macrocycle, however, it is important to preserve the amide framework. The macrocycle will be made up of 5- and 6-membered rings, in a 5,5,5,5 pattern, a 5,5,5,6, pattern, a 5,6,5,6 pattern, a 5,5,6,6, pattern, a 5,6,6,6 pattern, or a 6,6,6,6 ring pattern which will be described in more detail below.

A modified version of the method of the present invention adds protection/deprotection steps in order to generate the intermediate species. Functional groups of some starting materials may require protection during the acylation reaction of step one or the subsequent macrocyclization reaction to preserve some particular functionality. A deprotection step is then carried out before and/or after the macrocyclization step (step two of the primary method of the invention) to yield the final deprotected product. Techniques for protection and deprotection of a variety of functional groups are known to those skilled in the art. The particular techniques depend on the functional group and starting material of interest. The intermediate species (possibly in a protected form) are then coupled via a double coupling reaction analogous to that described above in order to generate the desired tetraamido macrocycle. Although the modified version of the method is in general longer and more complex, it provides a much wider range of macrocyclic tetraamide compounds due to the much greater degree of synthetic versatility that is conveyed by the use of protecting/activating groups.

Once the macrocyclic tetraamido ligand has been prepared, the macrocyclic compound may be complexed with a wide range of metal ions, preferably a transition metal, and most preferably a group VIA, VIIA, VIII or IB transition metal, to form a chelate complex of the formula wherein

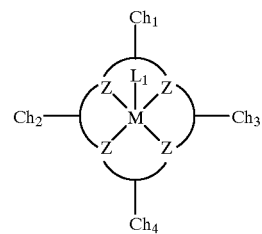

M is the metal, Z is N, $L_1$ is any labile ligand, $Ch_1$, $Ch_2$, $Ch_3$ and $Ch_4$ are oxidation resistant components of the chelate system which are the same or different and which, as stated above, form five- or six-membered rings with the adjacent ZMZ atoms.

Complexation is achieved by the following method. The macrocyclic ligand is dissolved in a supporting solvent, usually THF, and deprotonated by treatment with a base, preferably lithium bis-trimethylsilylamide, lithium di-isopropyl amide, t-butyl lithium, n-butyl lithium, or phenyl lithium. Any base that removes the amide N—H protons will suffice, but noncoordinating organic soluble bases are preferred. After the ligand is deprotonated, a metal ion is added. The resulting intermediate, a comparatively low valent ligand metal species, is then oxidized. The oxidation step is preferably performed with air, chlorine, bromine, or benzoyl peroxide to produce the metal chelate complex usually as a lithium salt. Metathesis of the resulting complex to form a tetraalkyl ammonium, tetraphenyl phosphonium or bis(triphenylphosphoranylidene) ammonium (PPN) salt tends to yield metal chelate complexes that are easier to purify as compared to the lithium ion containing complexes. The purified metal chelate complex, can then be used to catalyze oxidation reactions.

If the complex is then combined with a strong O-atom transfer oxidant, preferably a peroxide, such as hydrogen peroxide, t-butyl hydroperoxide, or cumyl hydroperoxide, a ligand-metal IV, V or VI oxo intermediate is produced. For cases in which oxidatively robust substituents have been employed to generate the ligand framework robust high oxidation state oxo containing species can be prepared, and it is believed that these high valent oxo containing species are the active transfer agents in catalyzing a number of oxidation reactions.

When a low valent metal species is exposed to a peroxide or other [O] containing oxidant the metal attracts and binds the oxygen from the oxidant. Depending on the metal, the bond between the metal and the oxygen will be very strong or may be only strong enough to remove the oxygen from the oxidant for subsequent transfer to another constituent.

If the metal is a metal III ion, the resulting oxo species will in general be a metal V ion. If the metal is a metal IV ion, the resulting oxo species will in general contain a metal VI ion. The combined stabilizing effect of the macrocyclic ligand and the participation of the d electron count at the metal center in controlling the degree of bonding to an oxo ligand tends to favor early transition metal complexes forming very strong oxygen-metal bonds to yield stable oxides. The middle and later transition metals tend to remove the oxygen from the oxidant, bind to the oxygen for a period of time and then transfer the oxygen to a substrate. In the metal ligand system produced by the method of the present invention, the middle and later transition metals, therefore, tend to promote the transfer of oxygen. In addition, to its stabilizing effect, the ligand also exerts influence on the metal properties. By controlling the metal, the electron density of the macrocycle, the charge on the complex, and the bond strength/bond order to the coordinated oxo ligand, the metal ligand complex can be fine tuned to achieve a complete range of oxygen transfer abilities, from stable oxides to high valent oxidation catalysts.

In the preferred embodiment, the axial ligand, $L_1$, is labile because it occupies its position relative to the metal until the chelate system is introduced into a solution containing an oxidant. The labile ligand will dissociate and will be replaced by the oxidant, most generally an O-atom transfer agent, but also any general oxidant that can serve to activate the metal ion to perform catalysis. Preferred labile ligands include, but are not limited to, the chloride anion, halide ions in general, $CN^-$, $H_2O$, $OH^-$, $ROH$, $NH_3$ or any amine, carboxylate, phenol or phenoxide, pyridine, ether, sulfoxide, ketone, or carbonate. The oxidation site in the metal complexes of aromatic-ring containing macrocycles can be manipulated by the choice of axial ligands as well as by the ring substituents.

As stated, the substituents on the components within the chelate system do not participate in the synthesis reaction so numerous variations are possible. If, for example, the ligand is to provide an oxidatively robust compound and catalyst, there are certain restrictions placed on the substituent. It is believed that hydrogen atom abstraction occurs between the malonate linker's substituents and the axial ligand bound to the central metal atom of the ultimate chelate system. The abstraction is believed to lead to oxidative degradation. The components of the chelate system are preferably selected from those having substituents that are resistant to oxidative degradation by virtue of having good bond strengths and/or of being comprised of species that have low conformational freedom to prevent attainment of conformers which are conducive to intramolecular oxidative degradation. Compounds which satisfy this criteria are described in co-pending U.S. patent application of T. J. Collins et al., for "Long-Lived Oxidation Catalyst Compounds", filed on even date herewith, the disclosure of which is hereby incorporated herein by reference. If oxidative degradation is not a concern, the components of the chelate system may be chosen from those having a much broader range of possible substituents.

The degree of resistance to oxidative degradation depends in part on the intended use of the resulting chelate system and catalyst. For example, if the reaction which the catalyst is intended to affect occurs early on in a process, a long lived catalyst may not be as critical. In that event, the substituent groups of the malonate starting material can have weaker bonds or exhibit conformational freedom. Examples include ethyl groups and longer chain alkyls. The activated oxalate or malonate derivative is believed to contribute to the most sensitive part of the resulting macrocylic ligand. The malonate may be unsubstituted, monosubstituted or disubstituted. Preferred substituent groups on the malonate include methyl, ethyl, halogen, hydrogen, $CF_3$ and a spirocyclopentyl or spiro-cyclohexyl ring in place of the disubstituted positions, $R_1$ and $R_2$.

DETAILED DESCRIPTION OF THE PREFERRED EMBODIMENTS

Figure 1:
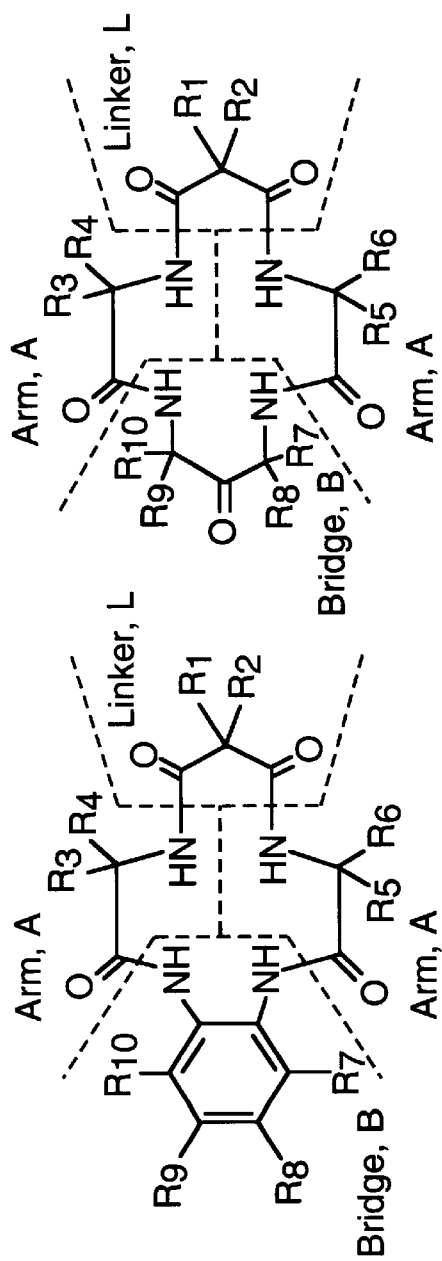
FIG. 1 is an example of substitution at the variable positions within the Bridge-Arm-Linker-Arm macrocyclic tetraamides described herein.

The primary method of the present invention provides a more efficient, less costly, higher yield synthesis of macrocyclic tetraamido ligands than has been heretofore available. Further, the primary method of the present invention permits the synthesis of a wide range of variants, many of which are difficult to synthesize via the prior art azide based synthetic method.

The primary method proceeds generally as shown in sequence 1. Sequence 2 shows a modified version of the primary method that employs protecting groups. Specific examples of the application of the primary method to the synthesis of some particular macrocyclic tetraamides are shown in sequence 3. For convenience of classification herein, the starting materials that are composed of diamine functionalities are sometimes referred to as "Bridges" (B), the starting materials composed of diacid functionalities are sometimes referred to as "Linkers" (L), and the starting materials composed of amine/acid functionalities are sometimes referred to as "Arms" (A). The arms of the macrocyclic compound are generally more resistant to degradative attacks than the linker.

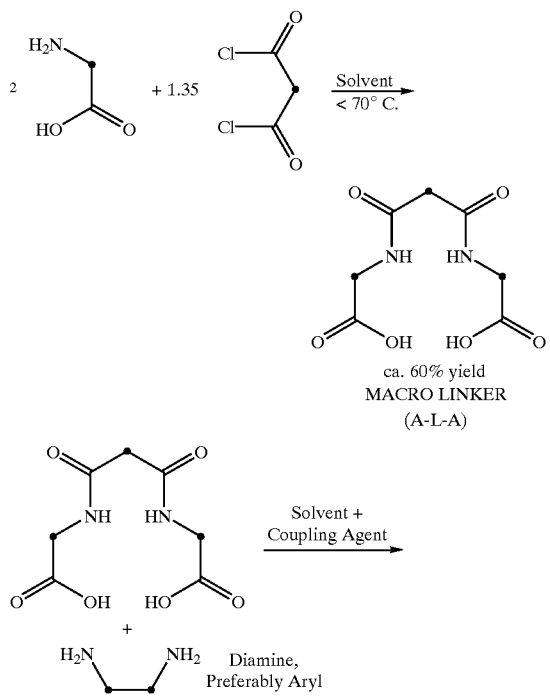

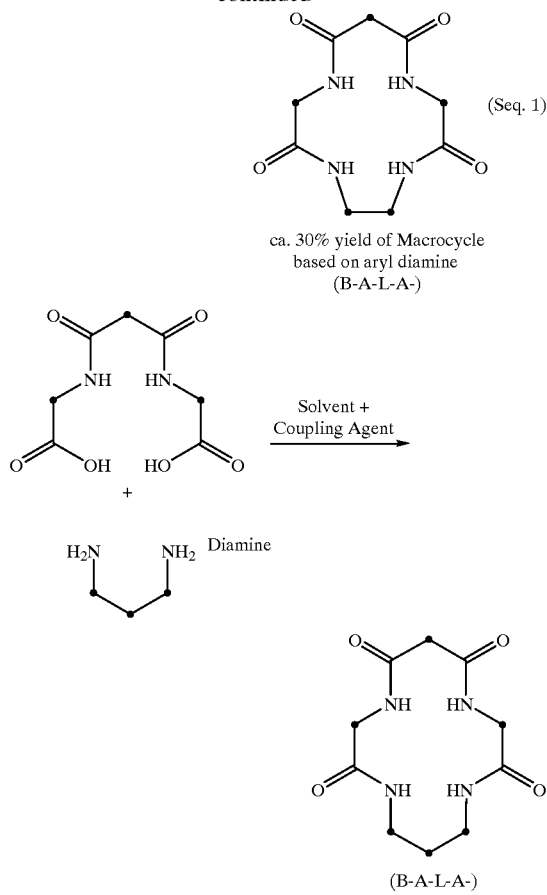

Sequence 1 is a generalized synthesis of macrocyclic tetraamides having a (B-A-L-A-) configuration, from α-amino carboxylic acids via the primary method of the invention. A diamide dicarboxyl-containing intermediate, sometimes referred to herein by the short hand designation, "macro linker intermediate" or simply the "intermediate" (A-L-A) is preformed without the use of protecting groups via a selective double coupling reaction wherein an α amino carboxylic acid, the arms, A, and an activated malonic acid derivative, the linker, L, in solvent are heated to form the macro linker intermediate. The macro linker intermediate is then coupled to a diamine, the bridge, B, in another selective double coupling reaction that employs a solvent, a coupling agent and heat. The synthetic methodology is highly streamlined and tolerates a wide range of functional groups. A wide range of macrocyclic tetraamides bearing different electronic or steric substituents have been prepared in this manner in good yield.

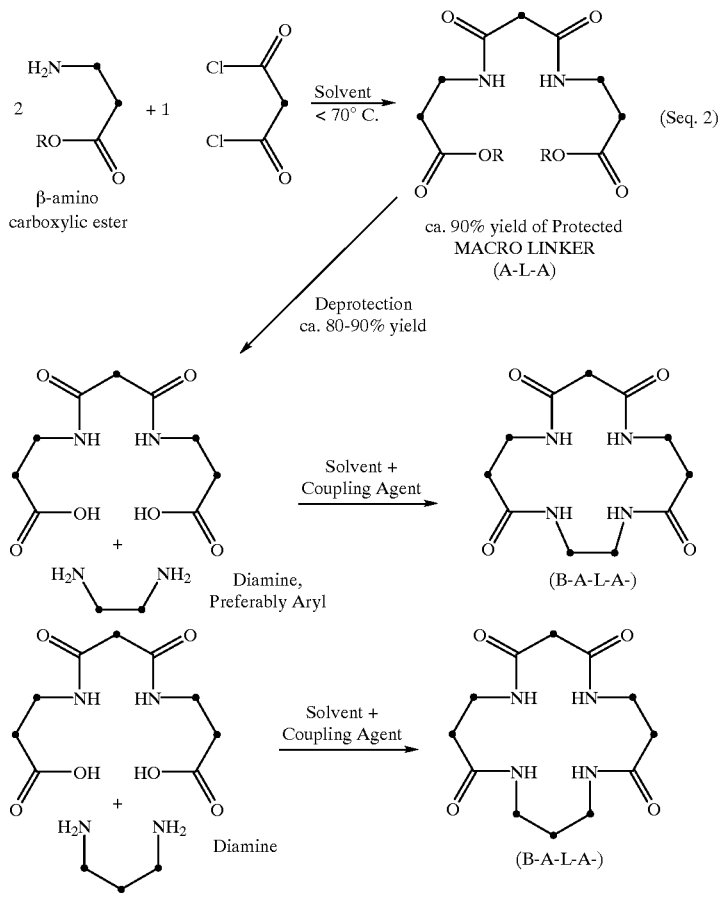

Sequence 2 is a generalized synthesis of macrocyclic tetraamides having a (B-A-L-A-) configuration, from β-amino carboxylic acids via a modified version of the primary method of the invention. The same basic approach employed with α-amino carboxylic acid starting materials is applied to β-amino carboxylic acid starting materials. For some amino carboxylic acids use of a protecting group may be desirable, as shown in sequence 2. A macro linker intermediate (A-L-A) is preformed via a selective double coupling reaction wherein a protected β-amino carboxylic ester arm, A, and an activated malonic acid derivative linker, L, in solvent are heated to form the intermediate, which after deprotection can then be coupled to the diamine bridge, B, in another selective double coupling reaction to yield a wide variety of substituted macrocyclic tetraamides with an expanded ring size compared to those that have been prepared from α-amino carboxylic acids.

The macro linker intermediate (A-L-A) can be made on a large scale in batch or continuous processing via direct reaction of a substituted malonyl dihalide with a solution (preferably a pyridine solution) of an α or β-amino carboxylic acid or ester. Many examples of the reaction proceed in good yield without the use of protecting groups at temperatures preferably less than or equal to about 70° C. Some examples may require the use of protecting groups and these reactions generally proceed in excellent yield. The intermediate can be separated into batches and each separate batch further reacted with a wide range of diamine bridging compounds having different steric or electronic substituents in the presence of a coupling agent. For the α-amino carboxylic acid case, the ring closing step proceeds for 48–120 hours and is ideally substantially moisture free, as in sequence 3. A wide range of tetraamido macrocycles having finely tuned electronic properties can be synthesized at a considerable cost savings over the prior art azide method.

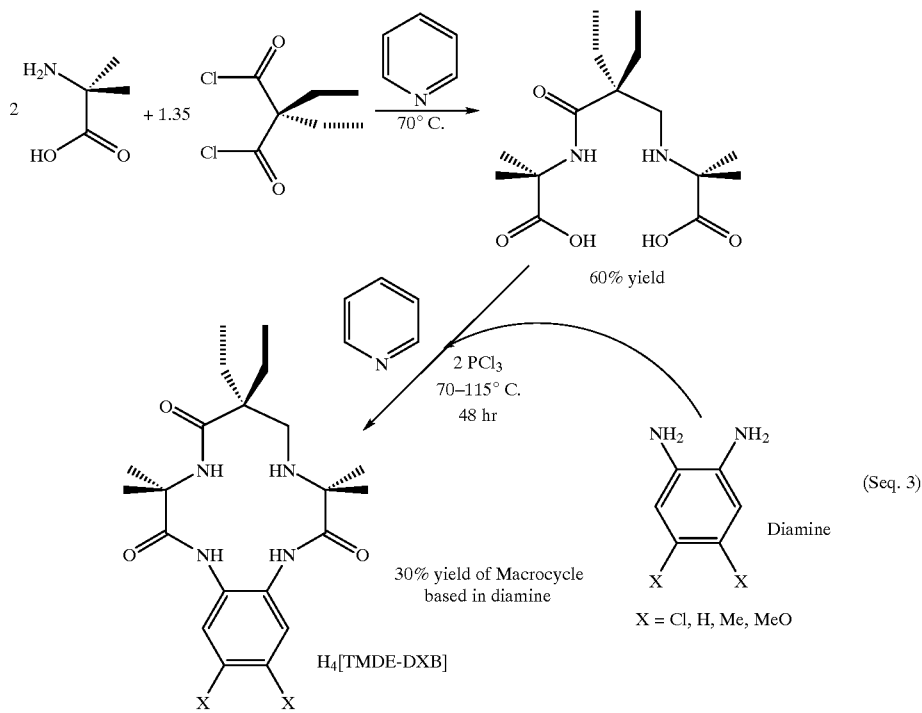

(Seq. 3)

Sequence 3 is a specific example of the preparation of macrocyclic tetraamides having a (B-A-L-A-) configuration from α-amino carboxylic acid starting materials. An α-amino carboxylic acid is mixed with an activated malonate in pyridine at temperatures less than 70° C. After the selective double coupling reaction is complete, 72–144 hrs, the macro linker intermediate (A-L-A) is isolated. In a second step a diamine, preferably an o-phenylene diamine, is added to a pyridine solution of the macro linker intermediate in the presence of a coupling agent, preferably $PCl_3$ or pivaloyl chloride. The ring closure, a double coupling reaction, is allowed to proceed at reflux for 48–110 hrs, and then the desired macrocyclic tetraamide is isolated in good yield.

The method of the present invention can be used to prepare the macrocyclic intermediate important to the synthesis of oxidatively robust macrocyclic tetraamides shown in Structure 1. The synthesis of oxidatively robust macrocyclic tetraamides requires that all H atoms α to the N-donor atoms be replaced by more oxidatively robust groups such as alkyl, halo, aryl or heterocyclic substituents.

Structure 1

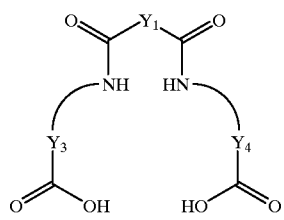

wherein $Y_1$, $Y_3$ and $Y_4$ each represent one, two or three carbon containing nodes for substitution, as explained in more detail herein, and wherein $Y_1$ also represents zero carbon containing nodes. Structure 1 shows the key intermediate for the method of the present invention, an oxidatively robust macro linker (Arm-Linker-Arm). This molecule can be readily synthesized in one step without the use of protecting groups.

In an alternative embodiment, the method of the invention uses protection/deprotection sequences to generate a protected form of the macro linker intermediate. Upon deprotection, the intermediate is coupled via the double coupling reaction described above to generate the tetraamido macrocycle. Similarly, protection/deprotection sequences can be applied to substituents present on the bridging unit to widen the range of bridging substituents that can be utilized in the macrocyclization reaction.

Both embodiments of the method of the invention rely heavily on the amine and carboxylic acid based starting materials hereinafter listed in Table 1. Table 1 lists several forms of the starting materials in what is designated the parent, protected/activated and hidden forms of the amine and carboxylic acid functionalities in a general sense.

TABLE 1

| Protected/<br>Activated<br>Amines | Hidden<br>Amines | Protected/<br>Activated<br>Carboxylic Acids | Hidden<br>Carboxylic Acids |
|---|---|---|---|
| N-alkyl amines | azides | activated esters | nitriles |
| amides | azo compounds | acyl halides | oxazolines |
| amino acetals | imides | amides | |
| N-benzyls | isocyanates | anhydrides | |
| carbamates | isothiocyanates | hydrazides | |
| enamines | nitrilium ions | O-acyl oximes | |
| hydrazines | nitro compounds | oxazolidines | |
| imines | phosphazos | oxazalones | |
| N-oxides | | phosphite esters | |
| N-phosphinyls | | silyl esters | |
| N-phosphoryls | | stannyl esters | |
| N-Metal | | substituted benzyl esters | |
| derivatives | | substituted ethyl esters | |
| silyl amines (N—Si) | | substituted methyl esters | |
| N-Sulfenyls | | sulfonyl esters | |
| 17sulfonamides | | sulfenyl esters | |
| N-Sulfonyls | | | |
| urea derivatives | | | |

As used herein "parent groups" (shown in italics in Table 1) define a preferred synthetic functionality. "Protected/activated groups" refers to those groups that contain an easily recognizable portion of the parent group. "Hidden groups" as used herein refers to those groups that need not contain an easily recognizable portion of the parent group but which are capable of ready conversion to the parent group or to a protected/activated form of the parent group. More detailed examples may readily be found in Greene and Greene, "Protective Groups in Organic Synthesis", John Wiley and Sons, New York (1981). An extensive list of protecting/activating groups particularly suitable for peptide synthesis may be found in G. A. Fletcher and J. H. Jones, "A List of Amino-Acid Derivatives Which are Useful in Peptide Synthesis", Int. J. Peptide Protein Res. 4, (1972), p.347–371. Common protection and deprotection steps for amines and carboxylic acids are shown schematically in Sequences 4(a)–(d) below.

(a) Protection of an Amine
(Acylation of an amine to form a trifluoroacetamide)

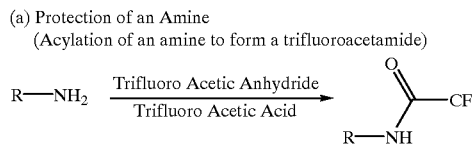

Seq. (4)

(b) Deprotection of an Amine
(Hydrolysis of a trifluoroacetamide to form an amine)

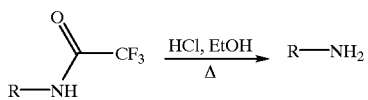

(c) Protection of a Carboxylic Acid
(Esterification of an acid to form an ester

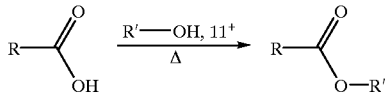

(d) Deprotection of a Carboxylic Acid
(Hydrolysis/Saponification of an ester to form an acid)

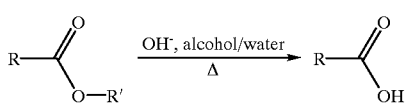

Some specific examples illustrating the utitlity of protecting groups are shown schematically in Sequence 5 below.

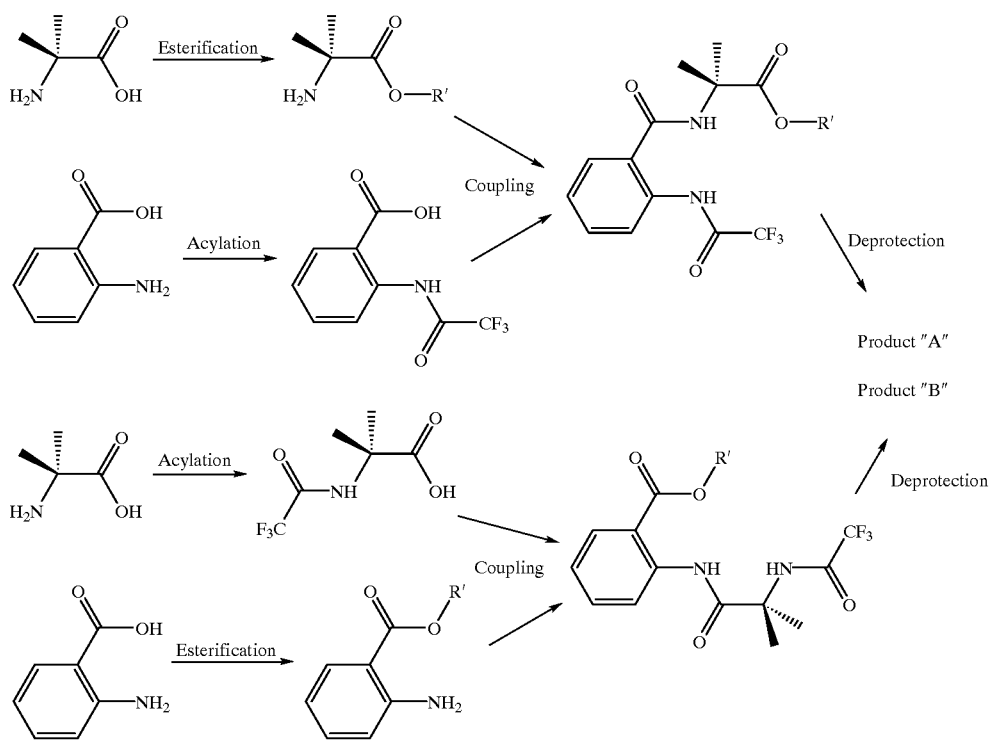

Seq. (5)

The categories shown in Table 1 are utilized in Table 2 in conjunction with chelation ring size constraints (5- and 6-membered chelate rings are preferred) in order to identify useful starting materials for the synthesis of chelating macrocyclic tetraamide compounds having the desired five- or six-membered ring-containing structure.

Structure 2 is used herein to define the shorthand notation shown in Table 2 and Table 3 that specifies the chelate ring sizes (including the metal ion) that are formed when a given macrocyclic ligand is coordinated to a transition metal center.

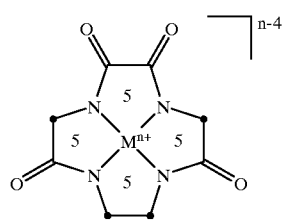

Structure 2

Structure 2 illustrates a (5,5,5,5) macrocyclic ligand shown in metal coordinated form with chelate ring sizes (including the metal ion) indicated. Using a counterclockwise rotation, the specific macrocycle employed is 5aa-5ca-5cc-5ac- (or any cyclic permutation thereof). Amine functionalities are indicated by (a) and carboxylate functionalities are indicated by (c). Dashes (—) indicate amide bonds. Every dash must connect a trailing "a" to a leading "c", or vice versa, the final dash wraps around to the beginning.

The parent (═) forms of the functional groups for each starting material are shown pictorially in Table 2 below, while possible combinations of protected/activated (p/a) or hidden (h) forms for each starting material are shown in tabular form. Variable positions are marked with a bullet (•). The underlined side captions are in a shorthand notation that refers to chelation ring sizes formed when the particular starting material is incorporated into a macrocycle and coordinated to a metal center.

TABLE 2

| $C_1$ | $C_2$ | $C_1$ | $C_2$ | $C_1$ | $C_2$ |
|---|---|---|---|---|---|
| ═ | ═ | p/a | ═ | h | ═ |
| ═ | p/a | p/a | p/a | h | p/a |
| ═ | h | p/a | h | h | h |

5cc: HOOC—COOH (positions 1, 2)

| $C_1$ | 2-N | $C_1$ | 2-N | $C_1$ | 2-N |
|---|---|---|---|---|---|
| ═ | ═ | p/a | ═ | h | ═ |
| ═ | p/a | p/a | p/a | h | p/a |
| ═ | h | p/a | h | h | h |

5ac: HOOC—CH(•)—NH₂ (positions 1, 2)

TABLE 2-continued

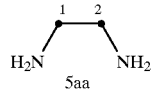

| 1-N | 2-N | 1-N | 2-N | 1-N | 2-N |
|-----|-----|-----|-----|-----|-----|
| =   | =   | p/a | =   | h   | =   |
| =   | p/a | p/a | p/a | h   | p/a |
| =   | h   | p/a | h   | h   | h   |

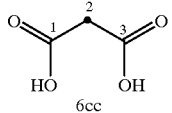

| $C_1$ | $C_3$ | $C_1$ | $C_3$ | $C_1$ | $C_3$ |
|-------|-------|-------|-------|-------|-------|
| =     | =     | p     | =     | n     | =     |
| =     | p/a   | p/a   | p/a   | n     | p/a   |
| =     | h     | p/a   | h     | h     | h     |

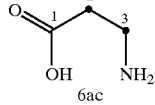

| $C_1$ | 3-N | $C_1$ | 3-N | $C_1$ | 3-N |
|-------|-----|-------|-----|-------|-----|
| =     | =   | p/a   | =   | h     | =   |
| =     | p/a | p/a   | p/a | h     | p/a |
| =     | h   | p/a   | h   | h     | h   |

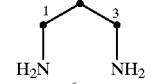

| 1-N | 3-N | 1-N | 3-N | 1-N | 3-N |
|-----|-----|-----|-----|-----|-----|
| =   | =   | p/a | =   | h   | =   |
| =   | p/a | p/a | p/a | h   | p/a |
| =   | h   | p/a | h   | h   | h   |

The complete range of macrocyclic tetraamide compounds able to be synthesized from the starting materials identified in Table 2 is shown in general terms in Table 3. Each of the 43 unique combinations has been listed pictorially and labelled with the shorthand notation of structure 2 defined above.

TABLE 3

12 membered tetraamide macrocycles (5,5,5,5)

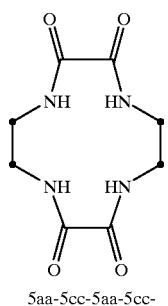

5aa-5cc-5aa-5cc-

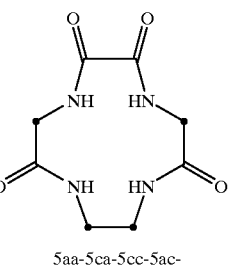

5aa-5ca-5cc-5ac-

TABLE 3-continued

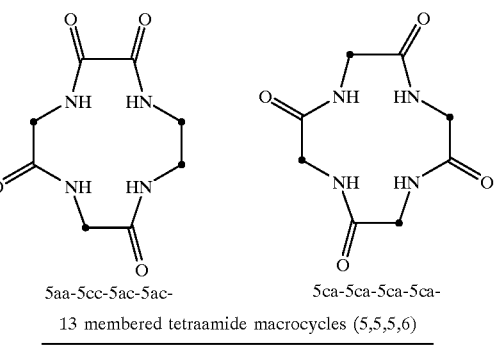

5aa-5cc-5ac-5ac-    5ca-5ca-5ca-5ca-

13 membered tetraamide macrocycles (5,5,5,6)

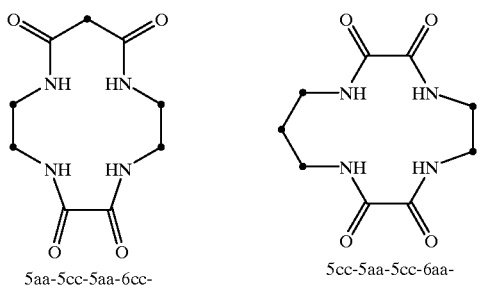

5aa-5cc-5aa-6cc-    5cc-5aa-5cc-6aa-

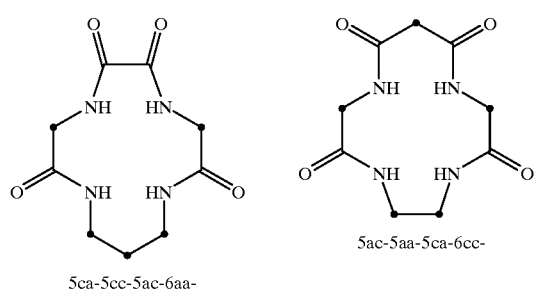

5ca-5cc-5ac-6aa-    5ac-5aa-5ca-6cc-

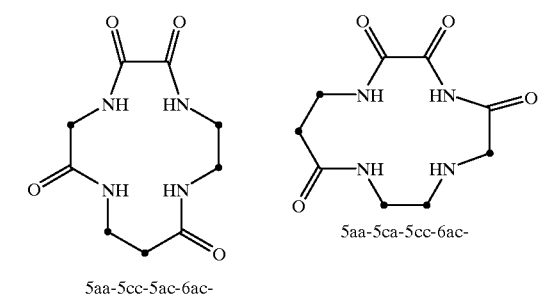

5aa-5cc-5ac-6ac-    5aa-5ca-5cc-6ac-

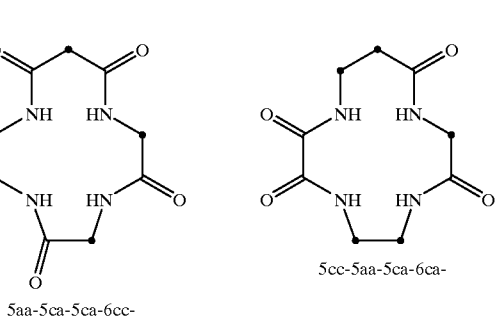

5aa-5ca-5ca-6cc-    5cc-5aa-5ca-6ca-

TABLE 3-continued
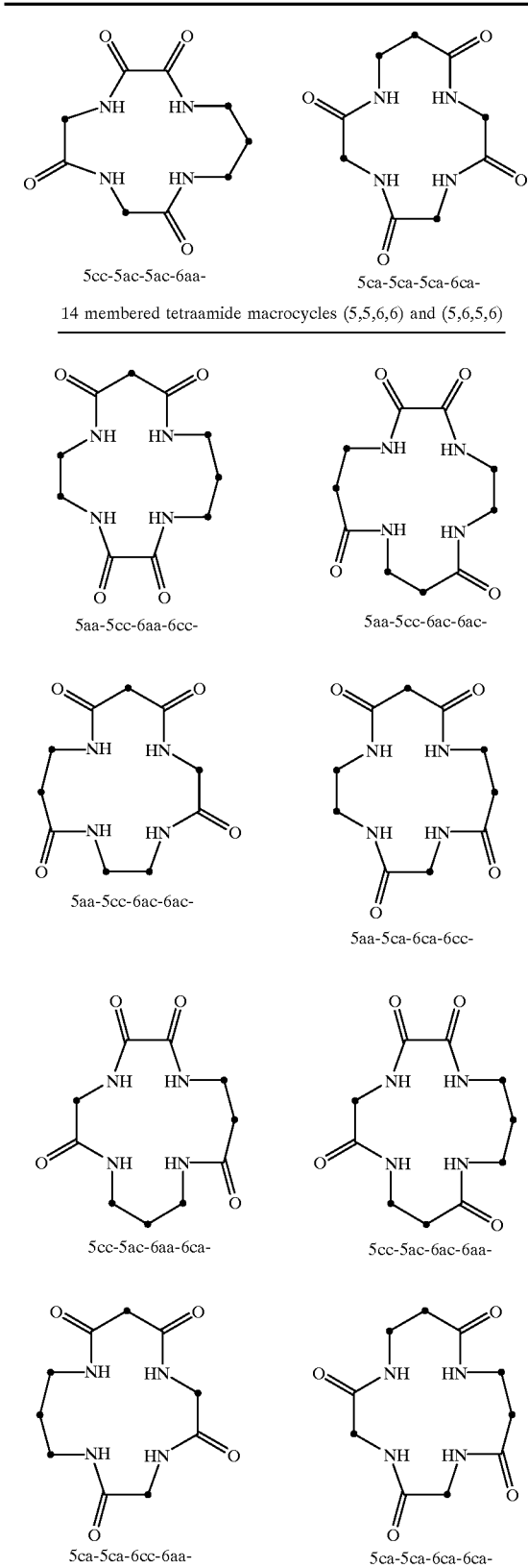
14 membered tetraamide macrocycles (5,5,6,6) and (5,6,5,6)
TABLE 3-continued
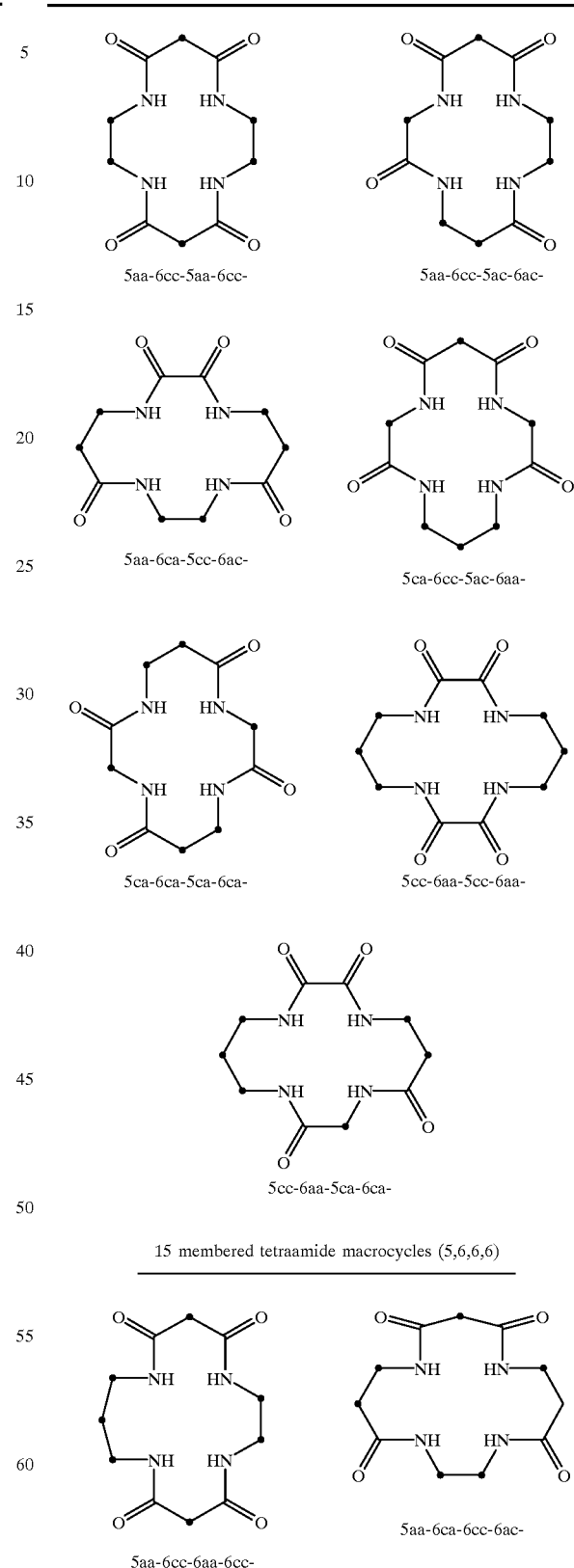
15 membered tetraamide macrocycles (5,6,6,6)

TABLE 3-continued

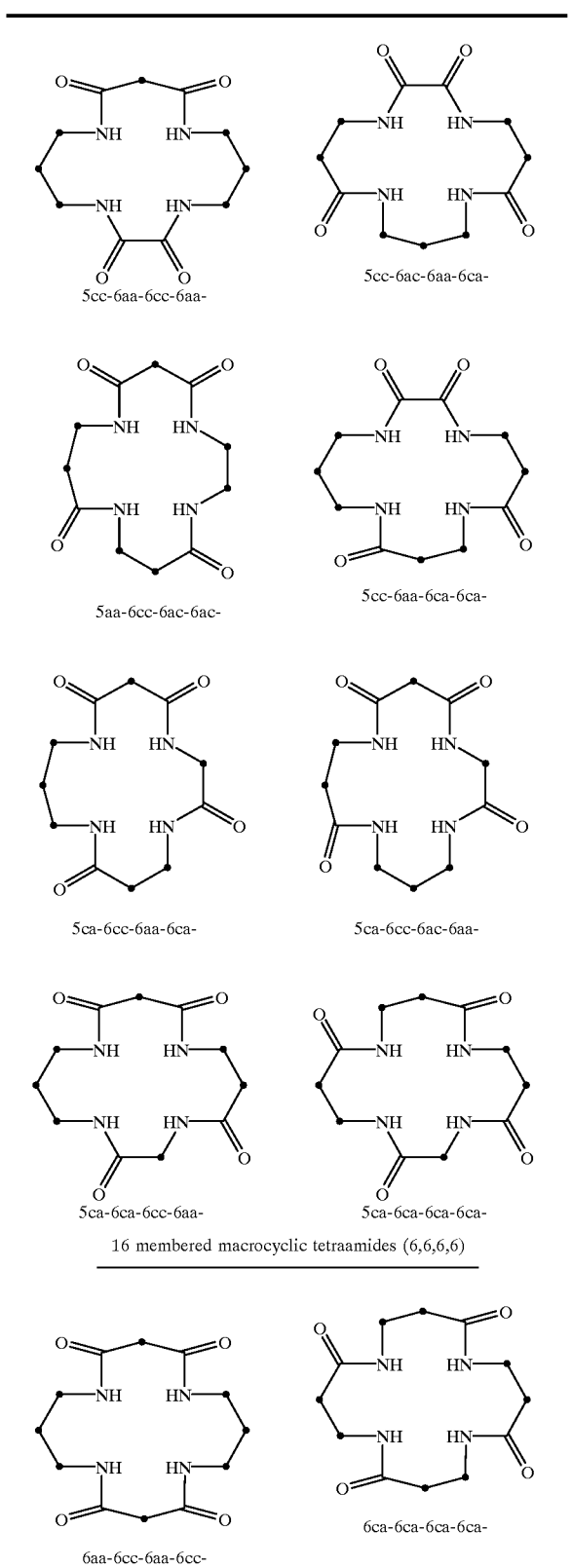

16 membered macrocyclic tetraamides (6,6,6,6)

TABLE 3-continued

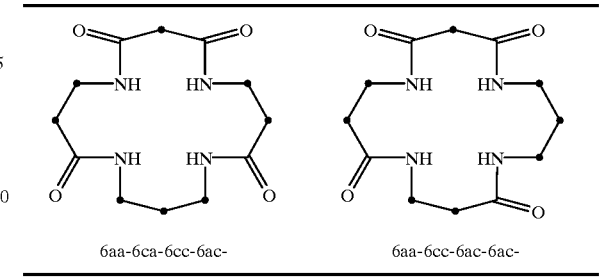

The individual Bridge, Arm and Linker starting materials can either be obtained commercially or synthesized by standard techniques. Examples of syntheses for a few non-commercially available starting materials are provided herein and in the Experimental Section. A powerful alternative route for the preparation of substituted and unsubstituted malonates has been reported by A. P. Krapcho, E. G. E. Jahngen, Jr. and D. S. Kashdan. "α-carbalkoxylations of carboxylic acids. A general synthetic route to monoesters of malonic acids", Tet. Lett. 32, p.2721–2723 (1974). The oxidatively robust macrocyclic tetraamides shown in Table 3 may be synthesized without having to resort to the use of high energy intermediates or species that contain high energy N—N bonds, such as hydrazines, azides and azo constituents.

Schematics 1 to 3 below pictorially demonstrate substitution at the variable positions shown by a ● in Table 3. The remainder of this section discusses how to choose R substituents in general terms, and lists some representative examples of substituted Bridge, Arm and Linker starting materials in tabular form. Finally a mathematical method for the enumeration of all of the different possible macrocyclic tetraamides that can be constructed within a given class from a given list of Bridge, Arm and Linker starting materials is presented (e.g. the lists of representative examples of substituted Bridge, Arm and Linker starting materials shown in Tables 4–6).

Single Node Substitution

Starting materials containing only one variable position are substituted by a carbon atom bearing two R groups, a —C($R_a$) ($R_b$)— unit, (in this context the dashes (—) refer to single bonds as opposed to amide bonds). See Schematic 1.

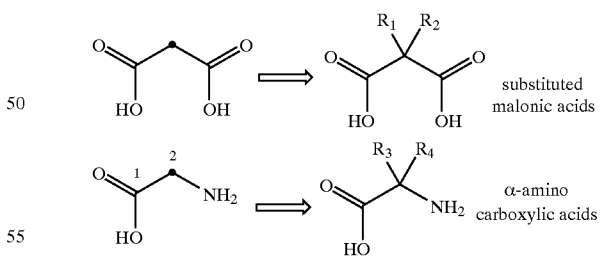

Schematic 1: Replacement of a single variable position is always by a —C($R_a$) ($R_b$)— unit.

For substitution at any single variable position the R groups on the —C($R_a$) ($R_b$)— unit may be the same or different and are selected from the group consisting of hydrocarbons and heteroatom (e.g., halogen, N, O, Si, P, S)

substituted hydrocarbons. Specific choices for the R groups are from the following types/subtypes either singly or in combination (e.g. for R=arylsilylester, only aryl, esters and siloxanes are listed); H, ketones, aldehydes, carboxylic acids, hidden or protected/activated carboxylic acids (see Table 1), esters, ethers, amines, hidden or protected/activated amines (see Table 1), imines, amides, nitro, sulphonyls, sulfates, phosphoryls, phosphates, silyl, siloxanes, alkyl, alkenyl, alkynyl, halo, aryl, and compounds chosen from biological systems e.g. natural or unnatural amino acid sidechains, heterocyclic rings, lactams, lactones, alkaloids, terpenes (steroids, isoprenoids), lipid or phospholipid chains.

For single node substitution, fusion of the $R_a$ and $R_b$ groups at a position that is not the site of substitution, but $\alpha$ to the site of substitution yields a species doubly bonded to the node such as an oxo (=O), imine (=NR$_a$), or a substituted vinyl group (=CR$_a$R$_b$). Formation of imines or substituted vinyl groups constitutes a form of nodal migration. If the original $R_a$ and $R_b$ groups are fused at a site that is not the site of substitution and is not $\alpha$ to the site of substitution then a cyclic ring structure is formed. If such cyclic groups are formed, additional R substituents on the cyclic groups are chosen in the same manner as for normal single node or multi node substitution (including the possibility of further R group fusions at one or more nodes to yield additional oxo, imine, substituted vinyl groups, or spiro, benzo, substituted benzo, heterocyclic, substituted heterocyclic, cycloalkyl, substituted cycloalkyl, cycloalkenyl or substituted cycloalkenyl ring structures). Preferred spiro/cyclic ring sizes are four, five or six membered rings.

Multi Node Substitution

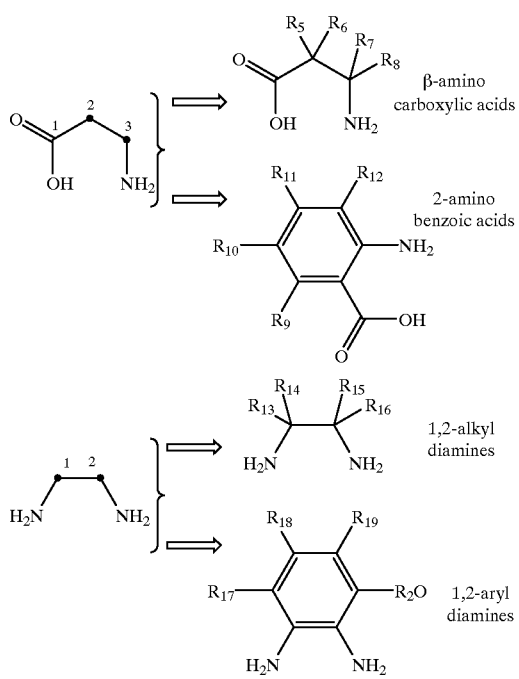

Schematic 2: Replacement at two variable positions can be by two —C(R$_a$) (R$_b$)— units or the two variable positions can be combined to make up part of an aryl or heterocyclic ring structure.

For multiple node substitution individual —C(R$_a$) (R$_b$)— positions are substituted identically as for single node substitution (see above). In addition to the types of substitution found for single nodes, it is also possible to combine or connect multiple nodes together via fusion of the R groups located on different nodes at sites that either are (combination), or are not (connection), the sites of attachment. Combination of sites that are adjacent leads to ethylenic units (—C(R$_a$)=C(R$_b$)—) a form of R group elimination. Connection of nodes via R group fusion at sites that are not the points of attachment or combination of sites that are not adjacent leads to the formation of cyclic structures, such as spiro, benzo, substituted benzo, heterocyclic, substituted heterocyclic, cycloalkyl, substituted cycloalkyl, cycloalkenyl or substituted cycloalkenyl ring structures. Four, five and six membered rings are preferred.

If cyclic groups are formed, or if there are residual R groups remaining from combination at adjacent sites, the residual R groups and the substituents on the cyclic groups are chosen in the same manner as for normal single node or multi node substitution (including the possibility of further R group fusions to yield additional spiro, benzo, substituted benzo, heterocyclic, substituted heterocyclic, cycloalkyl, substituted cycloalkyl, cycloalkenyl or substituted cycloalkenyl ring structures).

An important point is that the definitions for both single node and multi node substitution can function recursively, e.g. substituted o-phenylene diamine=>substituted heterocyclic o-phenylene diamine=>substituted spiro-cycloalkyl heterocyclic o-phenylene diamine etc.

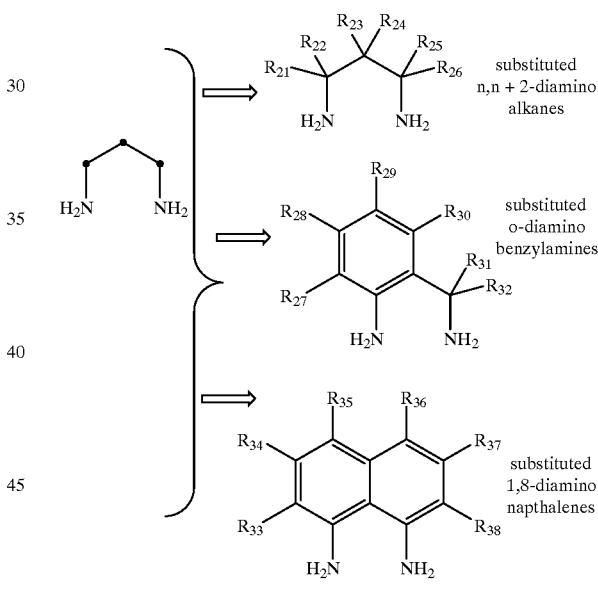

Schematic 3: Replacement at three variable positions can either be by three —C(R$_a$) (R$_b$)— units or two of the variable positions can be combined to make up part of an aryl or heterocyclic ring structure with the third position being replaced by a —C(R$_a$) (R$_b$)— unit or the three variable positions can all be combined to form part of a fused diaryl, fused aryl heterocyclic, or fused diheterocyclic ring structure.

Some representative examples of commercially available and/or synthetically versatile Linker, Arm and Bridge starting materials are shown in Tables 4, 5 and 6, respectively. A macrocyclic tetraamido compound having the desired chelate ring configuration shown in Table 3, i.e., 5555, 5556, 5656, 5566, 5666 or 6666, can be constructed by reference to the general choice and combination of starting materials for various chelate configurations shown in Table 2, i.e., parent, protected/activated or hidden, followed by the choice of the specific starting materials from Tables 4, 5 and 6. Use of those starting materials in the method of the present invention will provide a macrocyclic tetraamido compound having a chelate ring configuration and substituent array suited to a particular end use.

Table 4 identifies some representative dicarboxylic acid malonate or oxalate derivatives, i.e. Linkers, of interest for the preparation of macrocyclic tetraamides, either in parent, hidden, or protected/activated forms.

TABLE 4

The Oxalates and Malonates

Oxalates: Derivatives of Oxalic Acid (5cc)

| Registry # | Compound Name |
| --- | --- |
| | Oxalyl Chloride |

Malonates: Derivatives of Malonic Acid (6cc)

| Registry # | Compound Name | | Registry | Compound Name | |
| --- | --- | --- | --- | --- | --- |
| Disubstituted malonates ||||||
| 31696-00-1 | Diethyl | butylethylmalonate | | Diethyl | di-n-octylmalonate |
| 00596-76-9 | Diethyl | butylhexylmalonate | 24251-93-2 | Diethyl | di-n-pentylmalonate |
| 00083-27-2 | Diethyl | butylmethylmalonate | | Diethyl | di-2-propenyl malonate |
| | Diethyl | butylethylmalonate | 03195-24-2 | Diethyl | di-n-propylmalonate |
| | Diethyl | butylpentylmalonate | | Diethyl | ethylheptyl malonate |
| | Diethyl | butylpropylmalonate | | Diethyl | ethylhexylmalonate |
| | | "2,2-Diethylbutyric acid" | 00133-13-1 | Diethyl | ethyl(1-methylbutyl) malonate |
| 18719-43-2 | Diethyl | "1,1-cyclobutane dicarboxylate" | | Diethyl | ethylmethylmalonate |
| 53608-93-8 | Diethyl | "1,1-cyclopropane dicarboxylate" | 02049-70-9 | Diethyl | ethyl(1-methylpropyl) malonate |
| 01559-02-0 | Diethyl | decylethylmalonate | | Diethyl | ethylnonylmalonate |
| 05077-96-3 | Diethyl | decylmethylmalonate | 05408-35-5 | Diethyl | ethyloctylmalonate |
| | Diethyl | diallylmalonate | 00076-67-5 | Diethyl | ethylpentylmalonate |
| 03195-24-2 | Diethyl | dibenzylmalonate | | Diethyl | ethylphenylmalonate |
| 00597-55-7 | Diethyl | di-n-butylmalonate | 71691-56-0 | Diethyl | ethylpropylmalonate |
| 00596-75-8 | Diethyl | di-n-decylmalonate | | Diethyl | methyl(2-methylbutyl) malonate |
| | Diethyl | diethylmalonate | | Diethyl | methyl(2-methylpropyl) malonate |
| | Diethyl | di-n-heptylmalonate | 34009-61-5 | Diethyl | methylnonylmalonate |
| | Diethyl | di-n-hexylmalonate | 01575-67-3 | Diethyl | methylphenylmalonate |
| | Diethyl | dimethylmalonate | 58447-69-1 | Diethyl | methylpropylmalonate |
| 01619-62-1 | Diethyl | di-n-nonylmalonate | 00083-27-2 | Diethyl | methyl-iso-propylmalonate |
| | | "1,1-cyclopropane dicarboxylate" | | | "1,1-cyclobutane dicarboxylate" |
| | | "1,1-cyclopentane dicarboxylate" | | | "1,1-cyclohexane dicarboxylate" |
| | | ditrifluoromethyl malonic acid | | | ditrifluoroethyl malonic acid |
| | | dichloro malonic acid | | | dichloro malonic acid |
| Monosubstituted malonates ||||||
| | Diethyl | amylmalonate | 05398-10-7 | Diethyl | 5-hexenylmalonate |
| J6065-S9-4 | Diethyl | iso-amylmalonate | 10297-07-1 | Diethyl | n-hexylmalonate |
| 05398-08-3 | Diethyl | sec-amylmalonate | 05398-08-3 | Diethyl | 5-hexynylmalonate |
| 00117-47-5 | Diethyl | benzalmalonate | | Diethyl | iso-amylmalonate |
| 05292-53-5 | Diethyl | benzylidenemalonate | 05398-08-3 | Diethyl | iso-butylmethylmalonate |
| 05292-53-5 | Diethyl | benzylmalonate | 06802-75-1 | Diethyl | iso-pentylmalonate |
| 00607-81-8 | Diethyl | 2-benzylsuccinate | 00759-36-4 | Diethyl | iso-propylidenemalonate |
| | Diethyl | (4-bromobutyl)malonate | *58447-69-1 | Diethyl | iso-propylmalonate |
| 26971-92-6 | Diethyl | (2-bromoethyl)malonate | 00105-53-3 | Diethyl | isopropylmethylmalonate |
| 18721-64-7 | Diethyl | (7-bromoheptyl)malonate | 06335-37-1 | Diethyl | 4-methoxybenzal |
| | Diethyl | (6-bromohexyl)malonate | 00117-47-5 | Diethyl | 4-methoxybenzylmalonate |
| 29237-82-9 | Diethyl | (5-bromopentyl)malonate | | Diethyl | (1-methylbutyl)malonate |
| 01906-95-2 | Diethyl | (3-bromopropyl)malonate | 05398-08-3 | Diethyl | (2-methylbutyl)malonate |
| 10149-21-0 | Diethyl | 3-butenylmalonate | | Diethyl | (3-methylbutyl)malonate |
| | Diethyl | butylmalonate | 00609-08-5 | Diethyl | (1-methylhexyl)malonate |
| 00133-08-4 | Diethyl | (2-butyl)malonate | 14251-43-5 | Diethyl | methylmalonate |
| *00083-27-2 | Diethyl | iso-butylmalonate | 55898-43-6 | Diethyl | (2-methyl-2-propenyl)malonate |
| *10203-58-4 | Diethyl | sec-butylmalonate | 10203-58-4 | Diethyl | (1-methylpropyl)malonate |
| 00813-58-1 | Diethyl | (3-chloropropyl)malonate | 52180-01-5 | Diethyl | (2-methylpropyl)malonate |
| 03779-29-1 | Diethyl | 2-cyclopenten-1-yl malonate | 01472-85-1 | Diethyl | n-nonylmalonate |
| | Diethyl | n-decylmalonate | 01582-05-4 | Diethyl | n-octylmalonate |
| 00077-25-8 | Diethyl | "(3,4-difluorobenzyl)malonate" | 04475-07-4 | Diethyl | "(2,3,4,5,6-penta |
| | Diethyl | "2-(3,3-dimethylbutyl)malonate" | | | fluorobenzyl)malonate" |
| 06065-63-0 | Diethyl | n-dodecylmalonate | 06065-59-4 | Diethyl | 4-pentenylmalonate |
| 07252-87-1 | Diethyl | (2-ethylbutyl)malonate | | Diethyl | n-pentylmalonate |
| 25234-24-6 | Diethyl | ethylidenemalonate | | Diethyl | iso-pentylmalonate |
| 01462-12-0 | Diethyl | ethylmalonate | 06628-68-8 | Diethyl | 2-pentylmalonate |
| | Diethyl | (1-ethylpropyl)malonate | 02163-48-6 | Diethyl | (2-phenylethyl)malonate |
| 00685-88-1 | Diethyl | (4-fluorobenzyl)malonate | | Diethyl | propylmalonate |
| 00607-83-0 | Diethyl | fluoromalonate | | Diethyl | iso-propylmalonate |
| 41433-81-2 | Diethyl | n-heptylmalonate | | Diethyl | (3-trifluoromethylbenzyl)malonate |

TABLE 4-continued

The Oxalates and Malonates

Oxalates: Derivatives of Oxalic Acid (5cc)

| | | | | |
|---|---|---|---|---|
| 69298-59-5 | Diethyl n-hexadecylmalonate | 22390-04-1 | Diethyl | undecylmalonate |
| | | 1068-84-4 | | amino-malonic acid |

Unsubstituted malonates

| | | |
|---|---|---|
| 06768-23-6 | Diethyl | malonate |

Table 5 identifies some representative α and β amino carboxylic acids, i.e. Arms, of interest for the preparation of macrocyclic tetraamides, either in parent, hidden, or protected/activated forms.

TABLE 5

The Amino Carboxylic Acids
Derivatives of α-Amino Carboxylic Acids (5ac)

| Biological Amino Acids | Derivatives of Biological Amino Acids |
|---|---|
| glycine | |
| alanine | |
| valine (L-α-amino-isovaleric acid) | |
| leucine | ε-N, N, N-trimethyllysine |
| isoleucine | 3-methyl histidine |
| methionine | 5-hydroxy lysine |
| tryptophan | o-phosphoserine |
| serine | γ-carboxyglutamate |
| threonine | ε-N-acetyllysine |
| tyrosine | ω-N-methylarginine |
| cysteine | thyroxine |
| lysine | ornithine |
| arginine | β-cyanoalanine |
| histidine | homocysteine |
| asparagine (aspartic acid) | azaserine |
| glutamine (glutamic acid) | S-adenosylmethionine |
| phenylalanine (L-α-amino-β-phenyl propionic acid) | citrulline (L-2-amino-5-ureidovaleric acid) |

| Other Amino Acids | Other Amino Acids |
|---|---|
| (S)-2-amino-3-methoxypropionic acid | α-aminohydrocinnamonitrile |
| α-amino-β-methyl'aminopropionic acid hydrochloride | L-2-amino-4-hydroxy butyric acid |
| R(−)-2-amino-2-methyl butanedioic acid | (R,S)-2-amino-3-hydroxy-3-methyl butanoic acid |
| S(+)-2-amino-2-methyl butanedioic acid | (2S,3R)-2-amino-3-hydroxy-4-methyl pentanoic acid |
| S(+)-2-amino-2-methyl butanoic acid hydrate | DL-α-amino-β-hydroxy-valeric acid |
| 2-amino-2-methyl butyric acid | α-amino-β-imidazole propionic acid |
| 2-amino-3-methyl butyric acid | α-amino-γ-(3-indole) butyric acid |
| 2-amino-2-methyl glutaric acid | α-amino-β-ketoadipic acid methyl ester |
| 2-amino-5-methyl hexanoic acid | α-aminolauric acid |
| R(−)-2-amino-2-methyl-3-hydroxy propanoic acid | 2-amino-malonamide |
| S(+)-2-amino-2-methyl-3-hydroxy propanoic acid | 2-amino-3-mercapto propionic acid |
| 2-amino-7-methyl octanoic acid | (2S,3S)-2-amino-3-methoxy butanoic acid |
| (2S,4S)-2-amino-4-methyl pentanedioic acid | S(−)-2-amino-2-methyl-4-pentenoic acid monohydrate |
| (S)-2-amino-2-methyl-4-phosphonobutanoic acid | D-2-amino-4-methyl-5-phosphono-3-pentenoic acid |
| DL-2-amino-4(methylsulfonyl)butyric acid | S(−)-2-amino-3-(1-napthyl)propanoic acid |
| D-α-amino-nonylic acid | 2-amino-2-norbornane carboxylic acid |
| (+/−)α, -azelaic acid | 2-aminopelargonic acid |
| α-amino oleic acid | R(−)-α-aminophenyl acetic acid (D(−)-α-phenyl glycine) |
| L-2-amino-4-pentenoic acid (L-C-allyl glycine) | R(−)-2-amino-2-phenylbutyric acid |
| 2-amino-3-phenylbutanoic acid | L-2-amino-3-ureidopropionic acid (albizzin) |
| DL-2-amino-4-phenylbutyric acid | (2R,3S)-2-amino-3-phenylthiobutanoic acid hydrochloride |
| DL-2-aminovaleric acid (DL-norvaline) | (+)-2-amino-4-phosphonobutyric acid |
| D(−)-2-amino-5-phosphono pentanoic acid (D(−)-2-amino-5-phosphono | L(+)-2-amino-5-phosphono pentanoic |

TABLE 5-continued valeric acid)
D(−)-2-amino-4-phosphonobutyric acid
D(−)-2-amino-3-phosphono propionic acid
cis(+/−)-1-amino-3-phosphono cyclopentane carboxylic acid
L(+)-2-amino-7-phosphono heptanoic acid
DL-2-amino-8-phosphono octanoic acid
DL-α-amino-2-thiopheneacetic acid
DL-α-amino-3-thiopheneacetic acid
2-amino-4,4,4-trifluorobutyric acid
2-aminostearic acid
DL-2-amino suberic acid
L(+)-2-amino-6-(O,O' Diethylphosphono)hexanoic acid
L-2-amino-4-sulfamoyl butyric acid
L-2-amino-3-sulfamoyl propionic acid
DL-2-amino-7-sulfoheptanoic acid
D-α-amino adipic acid
L-α-amino adipic acid
(+/−)α,δ-diamino-adipic acid
L-α-amino-γ-bromo butyric acid
α-amino-isobutyric acid (a-methyl alanine)
D-α-aminobutyric acid
L-α-aminobutyric acid
D-2-amino caproic acid
D-α-amino caprylic acid
L-threo-α-amino-β-chlorobutyric acid
L(+)-2-amino-3-phosphono propionic acid
trans(+/−)-1-amino-3-phosphono cyclohexane carboxylic acid
D(−)-2-amino-7-phosphono heptanoic acid
DL-α-aminopimelic acid
(+/−)α,ω-diaminosuberic acid
acid (L(+)-2-amino-5-phosphono valeric acid)
cis(+/−)-1-amino-3-phosphono cyclohexane carboxylic acid
trans(+/−)-1-amino-3-phosphono cyclopentane carboxylic acid
D(−)-2-amino-6-phosphono hexanoic acid
DL-α-amino-hexanoic acid
1-aminocyclopropane-1-carboxylic acid
1-aminocyclobutane-1-carboxylic acid
1-aminocyclopentane-1-carboxylic acid (cycloleucine)
1-aminocyclohexane-1-carboxylic acid
2-aminodecanoic acid
α-amino succinic acid
(2S,3S)-2-amino-3-ethoxy butanoic acid hydrochloride
2-amino-3-fluoro butyric acid
L-α-amino-γ-guanidino butyric acid
L-α-amino-β-guanidino propionic acid
2-amino heptanoic acid
2-amino hexadecanoic acid
DL-2-amino hexanedioic acid
S(+)-2-amino-2-methyl-3-phenyl propanoic acid
L-2-amino-4-methyl-5-phosphono-3-pentenoic acid
2-amino-nonanoic acid
DL-α-amino-octanoic acid
(DL-α-aminocaprylic acid)
DL-2-amino-4-pentenoic acid
(DL-C-allyl glycine)
S(+)-α-aminophenyl acetic acid
(L(+)-α-phenyl glycine)
S(+)-2-amino-2-phenylbutyric acid
L-2-aminovaleric acid (L-norvaline)
cis-1-amino-3-(2-phosphonoacetyl) cyclobutane-1-carboxylic acid
L(+)-2-amino-6-phosphono hexanoic acid
(+/−)α,γ-diaminoglutaric acid Derivatives of β-Amino Carboxylic Acids (6ac)

| Registry # | Compound containing 2-amino-benzoic acid | Registry # | Compound containing 2-amino-benzoic acid |
|---|---|---|---|
| 118-92-3 | (o-amino-benzoic acid, anthranilic acid) | 118-92-3 | (o-amino-benzoic acid, anthranilic acid) |
| 619-17-0 | 4-nitro- | 3177-80-8 | 3-methoxy- |
| 616-79-5 | 5-nitro- | 6705-03-9 | 5-methoxy- |
| 4389-45-1 | 3-methyl- | 394-31-0 | 5-hydroxy- |
| 2305-36-4 | 4-methyl- | 4920-81-4 | 3-hydroxy- hydrochloride |
| 2941-78-8 | 5-methyl- | 446-32-2 | 4-fluoro- |
| 4389-50-8 | 6-methyl- | 446-08-2 | 5-fluoro- |
| 609-86-9 | 3,5-diiodo- | 434-76-4 | 6-fluoro- |
| 5653-40-7 | 4,5-dimethoxy- | | 4-chloro-5-sulfanoyl- |
| 50419-58-4 | 3,4-dimethyl- | 6388-47-2 | 3-chloro- |
| 14438-32-5 | 3,5-dimethyl- | 89-77-0 | 4-chloro- |
| 15540-91-7 | 3,6-dimethyl- | 635-21-2 | 5-chloro- |
| 2789-92-6 | 3,5-dichloro- | 2148-56-3 | 6-chloro- |
| 609-85-8 | 3,5-dibromo- | | 3-bromo-5-methyl- |
| | 3,5-dibromo-6-fluoro- | 1765-42-0 | 3,4,5,6-tetrafluoro- |
| | | 61948-85-4 | 3,4,5-trimethoxy- |

| Registry # | Other β-amino carboxylic acids | Registry # | Other β-amino carboxylic acids |
|---|---|---|---|
| | 3-amino-5-phenylthiophene-carboxamide | 5959-52-4 | 3-amino-2-napthoic acid |
| 5434-20-8 | 3-amino-pthalic acid | 5345-47-1 | 2-amino-nicotinic acid (2-aminopyridine-3-carboxylic acid) |
| 627-95-2 | b-amino-valeric acid hydrochloride | 82-24-6 | 1-amino-anthraquinone-2-carboxylic acid |
| | 2-amino-4-methyl-thiophene-3-carboxamide | 1664-54-6 | 3-amino-3-phenyl-propionic acid |
| | 2-amino-5-methyl-thiophene-3-carboxamide | 50427-77-5 | 5-amino-1-phenylpyrazole-4-carboxamide |
| 1068-84-4 | amino-malonic acid | | |

TABLE 5-continued

| | | | |
|---|---|---|---|
| 614-19-7 | β-amino-hydrocinnamic acid (D,L-3-amino-3-phenyl-propionic acid) | 72-40-2 | 5(4)-aminoimidazole-4(5)-carboxamide hydrochloride |
| 4507-13-5 | 2-amino-5-ethylthiophene-3-carboxylic acid, ethyl ester | 2627-69-2 | 5-amino-4-imidazole carboxamide riboside |
| 52834-01-2 | 2-amino-4,6-dimethyl-3-pyridinecarboxylic acid hydrochloride | 68302-09-0 | 2-amino-7-ethyl-5-oxo-5H-[1]benzopyrano[2,3-b]pyridine-3-carbonitrile |
| | | 22603-53-8 | 2-amino-3,5-dinitrobenzonitrile |
| 54711-21-6 | 5-amino-4-cyano-1-methyl-pyrazole | | 5-amino-4-cyano-1-(4-chlorophenyl)pyrazole |
| 698-29-3 | 4-amino-5-cyano-2-methyl pyrimidine | | 5-amino-4-cyano-1-(4-nitrophenyl) pyrazole |
| | 4-amino-5-cyano-2-methoxy pyrimidine | 16617-46-2 | 5-amino-4-cyano pyrazole |
| | | 21112-45-8 | β-amino-crotonic acid |
| 16750-40-6 | 3-amino-butyronitrile | 6375-47-9 | 3-amino-4-acetamido anisole |
| 82-24-6 | 1-aminoanthraquinone-2-carboxylic acid | 5424-01-1 | 3-amino pyrazine-2-carboxylic acid |
| 107-95-9 | 3-amino-propionic acid (β alanine) | 10312-55-7 | 2-amino terepthalic acid |
| 41680-34-6 | 3-aminopyrazole-4-carboxylic acid | 868-54-2 | 2-amino-1-propene-1,1,3-tricarbonitrile |
| | 2-amino-4,5,6,7-tetrahydrobenzo (b) thiophene-3-carboxylic acid ethyl ester | 584-20-3 | 3-amino-4,4,4-trifluorobutyric acid |
| 300-34-5 | 3-amino-L-tyrosine | | |
| 87550-19-4 | 3,6-dinitrophthalic acid pyridine salt | | |

Table 6 identifies some representative diamines, i.e. Bridges, of interest for the preparation of macrocyclic tetraamides, either in parent, hidden, or protected/activated forms. Amine and protected/activated or hidden amine functionalities are used interchangeably.

TABLE 6

The Diamines

Derivatives of 1,2-Aryl Diamines (5aa)

| Registry # | Compound containing o-Phenylenediamine | Registry # | Compound containing o-Phenylenediamine |
|---|---|---|---|
| | (1,2-Benzenediamine) No. of Unique Substituents = 1 | | (1,2-Benzenediamine) No. of Unique Substituents = 1 |
| 18645-88-0 | 3-fluoro- | 21745-41-5 | 3-chloro- |
| 367-31-7 | 4-fluoro- | 95-83-0 | 4-chloro- |
| 153505-39-6 | 3,4-difluoro- | 1668-01-5 | 3,4-dichloro- |
| 2369-29-1 | 3,5-difluoro- | 5233-04-5 | 3,5-dichloro- |
| 2369-30-4 | 3,6-difluoro- | 21732-93-4 | 3,6-dichloro- |
| 76179-40-3 | 4,5-difluoro- | 5348-42-5 | 4,5-dichloro- |
| 168966-54-9 | 3,4,5-trifluoro- | 30064-28-9 | 3,4,5-trichloro- |
| 363-74-6 | 3,4,6-trifluoro- | 1962-10-3 | 3,4,6-trichloro- |
| 2993-07-9 | 3,4,5,6-tetrafluoro- | 877-12-3 | 3,4,5,6-tetrachloro- |
| 1575-36-6 | 3-bromo- | 34446-43-0 | 3-iodo- |
| 1575-37-7 | 4-bromo- | 21304-38-1 | 4-iodo- |
| 1575-38-8 | 3,5-dibromo- | 144793-03-3 | 3,6-diiodo- |
| 69272-50-0 | 3,6-dibromo- | 76179-43-6 | 4,5-diiodo- |
| 49764-63-8 | 4,5-dibromo- | | |
| | No. of Unique Substituents = 2 | | No. of Unique Substituents = 2 |
| 75293-95-7 | 4-bromo-5-chloro- | 132915-81-2 | 3-chloro-4-fluoro- |
| 16429-44-0 | 5-bromo-3-chloro- | 153505-33-0 | 3-chloro-5-fluoro- |
| 172215-94-0 | 3-bromo-4,5-dichloro- | 139512-70-2 | 4-chloro-5-fluoro- |
| 98138-54-6 | 4-bromo-3,5-dichloro- | 153505-43-2 | 5-chloro-3-iodo- |
| 74908-80-8 | 3,5-dibromo-4-chloro- | 153505-34-1 | 3-chloro-4,5-difluoro- |
| 115440-10-3 | 3-bromo-5-fluoro- | 170098-84-7 | 4-chloro-3,5-difluoro- |
| 153505-37-4 | 4-bromo-5-fluoro- | 156425-14-8 | 4-chloro-3,5,6-trifluoro- |
| 153505-35-2 | 3-bromo-4,5-difluoro- | 153505-47-6 | 4,5-dichloro-3-iodo- |
| 156425-12-6 | 4-bromo-3,5,6-trifluoro- | 18225-92-8 | 3,4,6-trichloro-5-fluoro- |
| | | 153505-45-4 | 5-fluoro-3-iodo- |

TABLE 6-continued

The Diamines

| Registry Number | Additional 1,2-Benzenediamines | Registry Number | Additional 1,2-Benzenediamines |
|---|---|---|---|
| 88580-71-6 | 4,5-dimethyl-<br>4,5-dinitro-<br>4,5-dimethoxy-<br>4,5-diamino-<br>4,5-diacetamido-<br>4,5-ditrifluoromethyl-<br>4,5-dicyano-<br>4,5-dihydroxy | 615-72-5<br>59649-56-8 | 4-methyl-<br>4-nitro-<br>4-methoxy-<br>4-amino-<br>4-acetamido-<br>4-trifluoromethyl-<br>4-cyano-<br>4-hydroxy (3,4-diamino-phenol)<br>3-hydroxy (2,3-diamino-phenol) |
| | Other n,n+1-Diamines | | Other n,n+1-Diamines |
| 107-15-3 | ethylene diamine (1,2-diaminoethane)<br>1,1,2,2-tetramethyl ethylene diamine | 452-58-4<br>54-96-6 | 2,3-diamino pyridine<br>3,4-diamino pyridine<br>2-amino-3-nitro-5-bromo-pyridine |
| 7598-26-7 | 2-amino-3-nitro-5-methyl pyridine | | 4-amino-5-nitro-6-chlor-pyrimidine |
| 6635-86-5 | 2-amino-3-nitro-4-picoline (2-amino-4-methyl-3-nitro pyridine) | 7598-26-7 | 2-amino-3-nitro-9-fluorenone<br>2-amino-3-nitro-5-methyl-pyridine |
| 82039-90-5 | 5-amino-4-nitro-imidazole<br>5-amino-3-methyl-4-nitro-isoxazole<br>5-amino-1,3-dimethyl-4-nitro-pyrazole | 1672-48-6 | 4-amino-5-nitroso-uracil<br>6-amino-5-nitroso-2-thio-uracil<br>2-amino-5-bromo-3-nitro-pyridine |
| 6632-68-4 | 6-amino-1,3-dimethyl-5-nitroso-uracil | 33685-60-8 | 9,10-dinitro-anthracene<br>6,7-dinitro-2,3-diphenoxy-quinoxaline |
| 22603-53-8 | 2-amino-3,5-dinitro-benzonitrile | 35975-00-9 | 5-amino-6-nitro-quinoline |
| 3531-19-9 | 1-amino-2,4-dinitro-6-chlorobenzene | 771-97-1<br>938-25-0 | 2,3-diamino-napthalene<br>1,2-diamino-napthalene |
| 5442-24-0 | 4-amino-2,6-dihydroxy-5-nitro-pyrimidine<br>4-amino-2,6-diketo-1,3-dimethyl-5-nitroso-pyrimidine<br>1,2-dinitro-tetramethyl-benzene | 39070-63-8<br>68836-13-5 | 3,4-diamino-benzophenone<br>6,7-dinitro-quinoxaline<br>5,6-dinitro-quinoxaline-2,3-dione |
| 1436-59-5 | cis-1,2-diamino-cyclohexane<br>cis-1,2-diamino-cyclopentane<br>cis-1,2-diamino-1,2-dimethyl-cyclohexane<br>cis-1,2-diamino-1,2-dimethyl-cyclopentane | 2379-57-9<br>52057-97-3<br>1672-50-0<br>13754-19-3<br>3240-72-0 | 6,7-dinitro-quinoxaline-2,3-dione<br>3,4-diamino-5-hydroxy-pyrazole sulfate<br>4,5-diamino-6-hydroxy-pyrimidine<br>4,5-diamino-pyrimidine<br>4,5-diamino-uracil (5,6-diamino-uracil) |
| 36023-58-2 | 5,6-diamino-2,3-dicyano-pyrazine | | |
| 5440-00-6 | 5,6-diamino-1,3-dimethyl-uracil<br>5,6-diamino-3-methyl-uracil | | |
| 1758-68-5 | 1,2-diaminoanthraquinone | | |
| 6968-22-5 | 3-amino-4-nitro-benzoic acid | | |

Derivatives of n,n+2 Diamines (6aa)

| Registry # | n,n+2-diamines | Registry # | n,n+2-diamines |
|---|---|---|---|
| 4403-69-4 | 2-amino-benzylamine<br>2-amino-2-(2-aminophenyl)-propane | | 2,4-diamino-2,4-dimethyl-pentane-3-one<br>2,4-diamino-2,4-dimethyl-pentane |
| 109-76-2 | 1,3-diaminopropane | 479-27-6 | 1,8-diaminonapthalene |
| 3385-21-5 | 1,3-diaminocyclohexane<br>1,3-diamino-1,3-dimethylcyclohexane | 589-37-7<br>7328-91-8 | 1,3-diaminopentane<br>1,3-diamino-2,2-dimethyl propane |

The list of n, n+2-Diamines is significantly shorter than for the other derivatives, in large part because the syntheses of the required n,n+2 diamines are more complex than for the n, n+1 diamines.

In order to effectively discuss substitutions at all of the variable positions simultaneously, as in a substituted macrocyclic tetraamide compound, a sum over all of the possible combinations of the basic structural units may be constructed; bridges, B, arms, A, and linkers, L. This type of sum approach (a form of combinatorial analysis) provides a powerful method for the enumeration of all of the possible substituted macrocycles that can be constructed from any given list of substituted starting materials, for instance the lists previously cited. The combinatorial method proceeds as follows;

For any given class of macrocyclic tetraamides the connectivities of the bridge, arm and linker units is fixed e.g. Bridge-Arm-Linker-Arm-. Substitution at the variable positions then proceeds according to the rules stated previously. Some examples of the approach are shown in FIG. 1 and Eqn. 1. FIG. 1 shows some examples of substitution at the variable positions within the Bridge-Arm-Linker-Arm-group of macrocyclic tetraamides. The sum over all possible different combinations of bridges, B, arms, A, and linkers, L, is shown in Eqn. (1);

carboxylic acid equivalent (acid, ester, acyl chloride, nitrile etc. see Table 1).

The bridges and linkers of Table 7 conserve local two fold symmetry while all of the arms shown lead to 5 membered chelate rings, therefore although direct application of Eqn. (1) will yield 135 terms (5 bridges×3 arms×3 arms×3 linkers) some of the terms will be duplicates of molecules that have already been enumerated. Specifically the two fold symmetry allows for exchange of the arm positions; i.e. $B_iA_jL_kA_l = B_iA_lL_kA_j$. This allows Eqn.(2), a more concise form of Eqn.(1) that includes the effects of two fold symmetry, to be utilized to enumerate just the unique combinations.

$$\sum_{i,j \le l,k,l} B_i A_j L_k A_l \qquad \text{Eqn. (2)}$$

TABLE 7

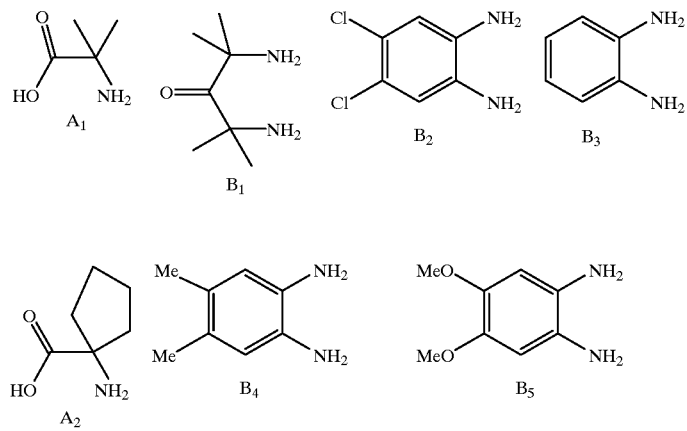

$$\sum_{i,j,k,l} B_i A_j L_k A_l \qquad \text{Eqn. (1)}$$

Asymmetric and/or chiral starting materials are accommodated in the numerical indices (i,j,k,l) of Eqn. (1) through enumeration of the different internal arrangements of R groups within the bridges, arms and linkers. Some specific examples of bridge, arm and linker starting materials are shown in Table 7. In each case the amide bonds have been retrosynthetically decomposed to form an amine equivalent (amine, nitro, azide, isocyanate, etc. see Table 1) and a Some specific Bridge, B, Arm, A, and Linker, L, starting materials.

The 90 unique combinations arising from application of Eqn.(2) to the B, A, and L units of Table 7, are shown in Table 8. Synthetic details for the preparation of many of the examples listed in Table 8 are given in the experimental section. Table 8 provides an enumeration of the group of 90 macrocyclic tetraamido molecules able to be constructed from the starting materials of Table 7 with application of Eqn.(2).

TABLE 8

| B₁A₁L₁A₁ | B₁A₁L₁A₂ | B₁A₁L₁A₃ | B₁A₂L₁A₂ | B₁A₂L₁A₃ | B₁A₃L₁A₃ |
|---|---|---|---|---|---|
| $B_1A_1L_2A_1$ | $B_1A_1L_2A_2$ | $B_1A_1L_2A_3$ | $B_1A_2L_2A_2$ | $B_1A_2L_2A_3$ | $B_1A_3L_2A_3$ |
| $B_1A_1L_3A_1$ | $B_1A_1L_3A_2$ | $B_1A_1L_3A_3$ | $B_1A_2L_3A_2$ | $B_1A_2L_3A_3$ | $B_1A_3L_3A_3$ |
| $B_2A_1L_1A_1$ | $B_2A_1L_1A_2$ | $B_2A_1L_1A_3$ | $B_2A_2L_1A_2$ | $B_2A_2L_1A_3$ | $B_2A_3L_1A_3$ |
|  | $B_2A_1L_2A_2$ | $B_2A_1L_2A_3$ | $B_2A_2L_2A_2$ | $B_2A_2L_2A_3$ | $B_2A_3L_2A_3$ |
| $B_2A_1L_2A_1$ | | | | | |
| $B_2A_1L_3A_1$ | $B_2A_1L_3A_2$ | $B_2A_1L_3A_3$ | $B_2A_2L_3A_2$ | $B_2A_2L_3A_3$ | $B_2A_3L_3A_3$ |
| $B_3A_1L_1A_1$ | $B_3A_1L_1A_2$ | $B_3A_1L_1A_3$ | $B_3A_2L_1A_2$ | $B_3A_2L_1A_3$ | |
| | | | | | $B_3A_3L_1A_3$ |
| $B_3A_1L_2A_1$ | $B_3A_1L_2A_2$ | $B_3A_1L_2A_3$ | $B_3A_2L_2A_2$ | $B_3A_2L_2A_3$ | $B_3A_3L_2A_3$ |
| $B_3A_1L_3A_1$ | $B_3A_1L_3A_2$ | $B_3A_1L_3A_3$ | $B_3A_2L_3A_2$ | $B_3A_2L_3A_3$ | $B_3A_3L_3A_3$ |
| $B_4A_1L_1A_1$ | $B_4A_1L_1A_2$ | $B_4A_1L_1A_3$ | $B_4A_2L_1A_2$ | $B_4A_2L_1A_3$ | $B_4A_3L_1A_3$ |
| $B_4A_1L_2A_1$ | $B_4A_1L_2A_2$ | $B_4A_1L_2A_3$ | $B_4A_2L_2A_2$ | $B_4A_2L_2A_3$ | $B_4A_3L_2A_3$ |
| $B_4A_1L_3A_1$ | $B_4A_1L_3A_2$ | $B_4A_1L_3A_3$ | $B_4A_2L_3A_2$ | $B_4A_2L_3A_3$ | $B_4A_3L_3A_3$ |
| $B_5A_1L_1A_1$ | $B_5A_1L_1A_2$ | $B_5A_1L_1A_3$ | $B_5A_2L_1A_2$ | $B_5A_2L_1A_3$ | $B_5A_3L_1A_3$ |
| $B_5A_1L_2A_1$ | $B_5A_1L_2A_2$ | $B_5A_1L_2A_3$ | $B_5A_2L_2A_2$ | $B_5A_2L_2A_3$ | $B_5A_3L_2A_3$ |
| $B_5A_1L_3A_1$ | $B_5A_1L_3A_2$ | $B_5A_1L_3A_3$ | $B_5A_2L_3A_2$ | $B_5A_2L_3A_3$ | $B_5A_3L_3A_3$ |

Entries shown with bold face and a solid box in Table 8 are shown specifically in the structures below.

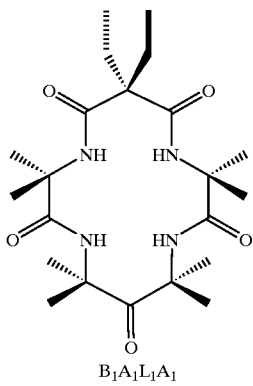

$B_1A_1L_1A_1$

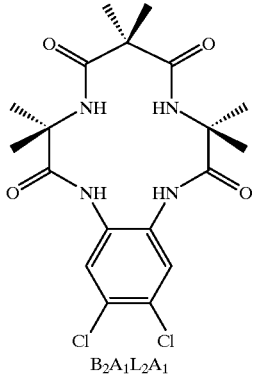

$B_2A_1L_2A_1$

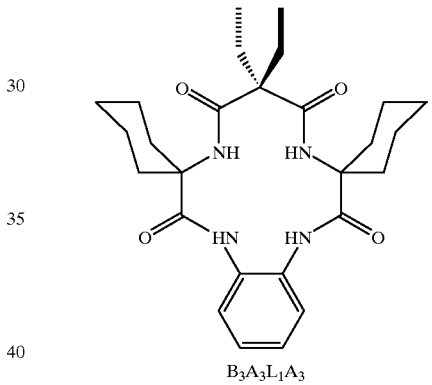

$B_3A_3L_1A_3$

These structures provide a few specific examples of macrocyclic tetraamides that have been constructed from the starting materials of Table 7 via the method of the present invention. The captions utilize a running numerical index to indicate the position of the specific starting material in a given list of possible starting materials, e.g. $B_2$ refers to the second Bridge in some specified list of Bridges. See, Eqn 1.

Since numerous variations of substituted $\alpha$ and $\beta$ amino acids, activated malonate derivatives and substituted diamines are available commercially or can be easily made by known techniques, macrocyclic compounds having a much wider variety of substituents can be synthesized easily by the method of the present invention than heretofore possible by the prior art azide method.

Treatment of the macrocyclic tetraamides with strong noncoordinating bases and exposure to transition metal salts leads to the formation of chelate compounds possessing four amido-N to metal bonds. When placed in an oxidizing media these chelate compounds can function as robust oxidation catalysts. As used herein, robust oxidation catalyst means that when the catalyst is added to a solvent in the presence of an oxidant, such as a peroxide, the half-life of the activated form of the metal complex is 30 seconds or more. The half-life is the time in which half of the metal complex decomposes or degrades. A preferred design for producing robust ligands is a macrocyclic tetraamido ligand having no hydrogens α to the N-amido donor groups.

A preferred tetraamido macrocycle prepared by the method of the invention has the following structure:

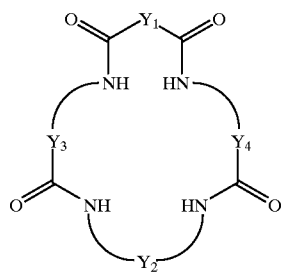

wherein $Y_1$ to $Y_4$ each represent one, two or three carbon containing nodes for substitution and Y, can also represent zero carbon containing nodes. Each node is a C(R) or C(R)$_2$ wherein each R substituent is the same or different, pairwise and cumulatively, from the remaining R substituents and is selected from the group consisting of alkyl, or alkenyl, aryl, hydrogen, halogen, CF$_3$ and combinations thereof or any of the substituents referenced herein, or together with a paired R substituent bound to the same carbon atom form a cyclopentyl or cyclohexyl ring. Pairs, particulary pair, $R_1$, $R_2$, of $Y_1$, may be nonlinked, or linked to form a spiro/cyclo form of substituent.

$Y_2$ is preferably selected from the group consisting of

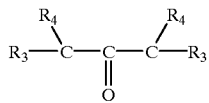

(i)

wherein $R_3$ and $R_4$ are the same or different, pairwise and cumulatively, and are alkyl, aryl, hydrogen, halogen, CF$_3$, or any of the substituents referenced herein; and (ii) a substituted aryl group comprised of $C_6H_2X_2$, $C_6H_3X$, $C_6HX_3$, $C_6X_4$, $C_5H_3N$, $C_4H_2N_2$, wherein X is halogen, hydrogen, alkyl, aryl, NH$_2$, methyl, CHO or any of the substituents referenced herein.

The R substituents of the structures shown above are more particularly selected from the substituents containing hydrogen, ketones, aldehydes, carboxylic acids, hidden or protected/activated carboxylic acids, esters, ethers, amines, hidden or protected/activated amines, imines, amides, nitro, sulphonyls, sulfates, phosphoryls, phosphates, silyl, siloxanes, alkyl, alkenyl, alkynyl, halo, and aryl.

Macrocycles with spiro-cyclohexyl substituents have been prepared by the present method and found to render the macrocycle very hydrophobic. Long chain substituents, such as a dodecyl chain, or phospholipid chain will render the macrocycle soluble in membranes.

The spiro-cyclohexyl derivative is sterically hindered and has slower reaction rates than the other preferred substituents, so the normal synthesis of the amide intermediate of the first step of the method of the invention is altered.

Synthesis of the bis spiro-cyclohexyl macro linker intermediate was accomplished by adding acylating agent dropwise in multiple aliquots, preferably three, separated in time. Twelve hour intervals followed by extended reaction periods produced the best results. Without the extended reaction periods, the yield was lower. The reaction sequence is shown in thr sequences below. Cyclohexane can be used to separate the oxazalone form of the macro linker away from the other reaction products, or water can be added to hydrolyze the oxazalone in situ. Hydrolysis of the intermediate oxazalones provides an increased yield of the desired bis cyclohexyl product.

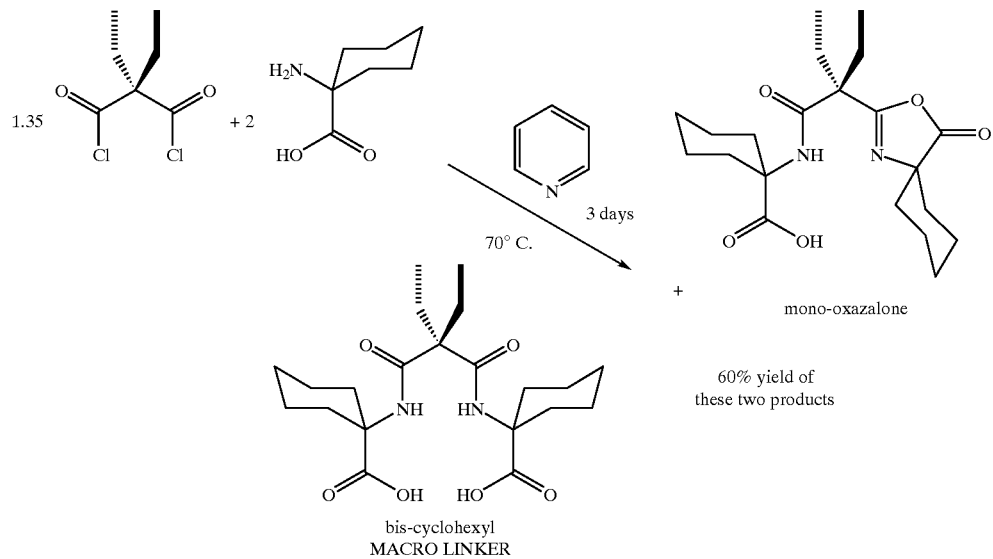

Synthesis of a bis spiro-cyclohexyl macro linker.

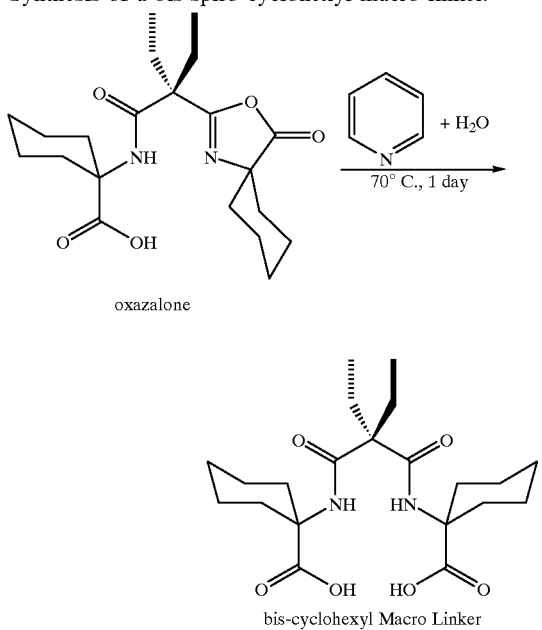

oxazalone bis-cyclohexyl Macro Linker

Hydrolysis of a hydrophobic oxazalone

The cyclohexyl-containing macro linker is then ready for ring closure in the same manner as other amide intermediates of the primary method of the invention. However, due to the enhanced stability of the spiro-cyclohexyl containing macrocyclic intermediates, separation of the macrocycle from reaction by-products differs from other preferred ring closing constituents. Typically, the crude macrocyclic product is extracted into an organic solvent, such as $CH_2Cl_2$. The $CH_2Cl_2$ solution is washed with acids and bases to remove the impurities and side products that contain acidic and basic functionalities and to hydrolyze any oxazalone containing intermediates. The cyclohexyl tetraamido macrocycle is not well purified by the usual acid/base washes yielding instead an approximately 1:1 mixture of the bis cyclohexyl oxazalone and bis-cyclohexyl tetraamido macrocycle. Pentane extraction of the mixture yields a clean separation. The macrocycle is insoluble and isolated as a powder, while the pentane soluble fraction can be evaporated to yield large crystals of the bis cyclohexyl oxazalone.

Table 9 shows the dependence of the yield on the amount of diethyl malonyl dichloride used in the synthesis of some macro linker intermediates (Arm-Bridge-Arm).

Figure 2:
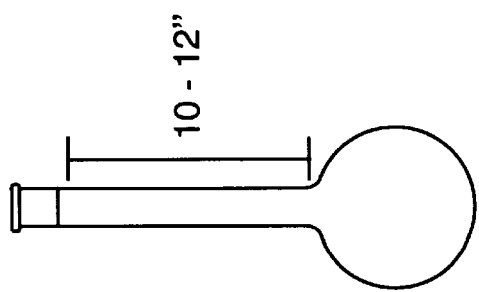
FIG. 2 is an illustration of a long necked RB flask used for controlling the atmosphere of the macrocyclization reactions of the present invention at reflux temperatures greater than 100° C.

Addition of an excess of the substituted malonyl dichloride improves the yield of macro linker with an optimum ratio of about 2 moles of amino acid to 1.35 to 1.5 moles of the substituted malonyl dichloride. The product mixture includes the macro linker and a mono oxazalone form of the macro linker which can be readily hydrolysed to yield additional product. The yield of the method is improved significantly if water is excluded from the reaction solution during ring closure reactions. FIG. 2 illustrates an original design for a long-necked RB flask utilized in the ring closure step of the primary method of the invention. This type of air cooled condenser is preferred for performing lengthy macrocyclization reactions in refluxing high boiling (b.p. >100° C.) solvents. A clamp placed halfway up the neck not only serves to secure the flask and its contents but also acts as an additional heat sink to prevent hot solvent vapor from rising too high up the neck. In a normal reflux apparatus, the joints are located much closer to the RB flask and the hot solvent vapors can readily melt/dissolve the grease in the fittings or leak past TEFLON joint sleeves.

Pyridine diamines can also be utilized. The prior art azide synthetic route, which includes a reduction step that also reduces the pyridine ring, does not yield a macrocyclic compound having a pyridine bridge. Amino pendant variations would also be tedious to synthesize by the prior art method. The amino pendant variations are of considerable interest because they permit the macrocyclic compound or metallocomplex to be tethered to a support, such as a polymer or sand, or to other molecules or substrates having functional groups which will covalently bond with the amine. Groups which covalently bond with amines are well known in the art and include in complexed form, for example, alkyl amines, amides, sulphonamides, imines, and other hidden or protected/activated forms, see Table 1.

The synthesis of the aryl amino pendant macrocycle proceeds generally as in Sequences 6 and 7.

TABLE 9

Yields of some macro linker materials under different synthetic conditions.

| MACRO LINKER | Yield of MACRO LINKER (not including oxazalones) | Yield with hydrolysis of oxazalones to MACRO LINKER | Moles of amino acid: moles of diethyl malonyl dichloride | | |
|---|---|---|---|---|---|
| | | | 2:1 | 2:1.35 | 2:2 |
| TMDE | 20–30% | | X | | |
| TMDE | 40–50% | 60–65% | | X | |
| Cyclohexyl | | 70–75% | | | X |

Seq. (6)

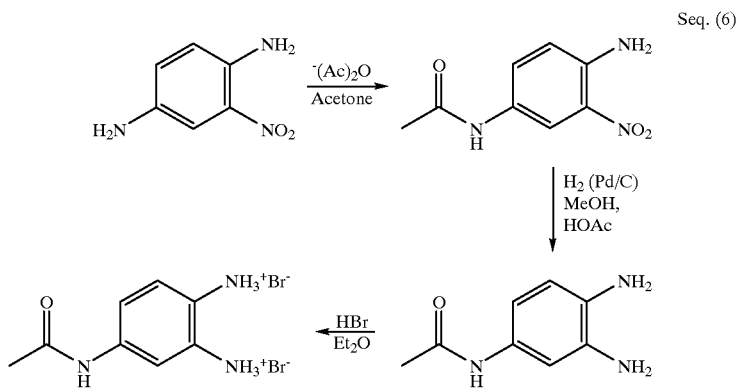

Synthesis of 1,2-Diamino-4-Acetamidobenzene (dihydrobromide)

Note the strategic and selective introduction of a protected amino group (an acetamide) onto the aryl diamine group (Bridge). The protected form of the bridge, an acetamide diamine, is then suitable for ring closure via the standard diamine+intermediate linker synthetic routes described herein. An extended ring closure time is required to achieve macrocyclization and is attributed to unfavorable hydrogen bond formation between the attached oxazalone and the acetamido group, which would be expected to slow down the desired macrocyclization reaction.

Once the protected amino pendant macrocycle has been synthesized as in sequence 5, it can be metallated with cobalt. Removal of the acetyl protecting group then yields a macrocyclic cobalt complex that is ready to be attached to a support. Best results to date have been obtained by reacylating the pendant amino group with acryloyl chloride to yield an amide linked vinyl pendant macrocycle.

Seq. (7)

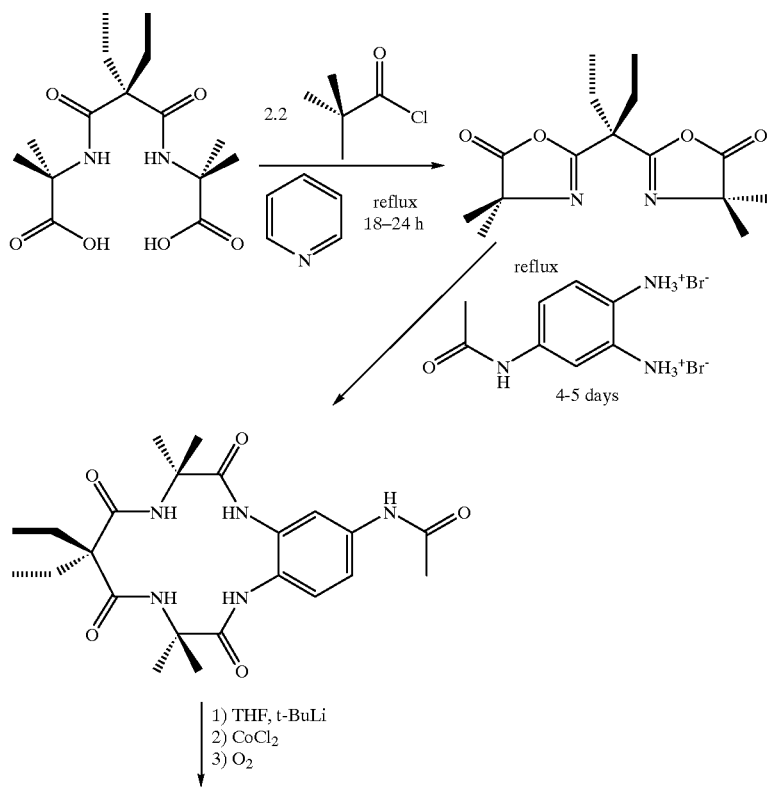

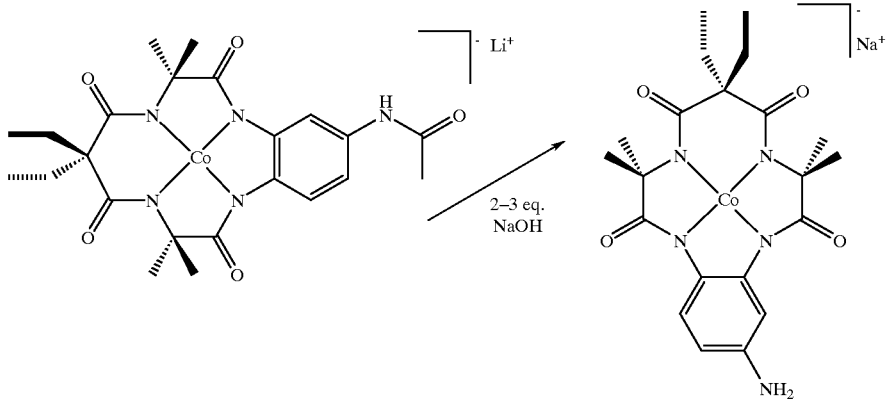

Synthesis of an amino pendant macrocyclic cobalt complex

Figure 3:
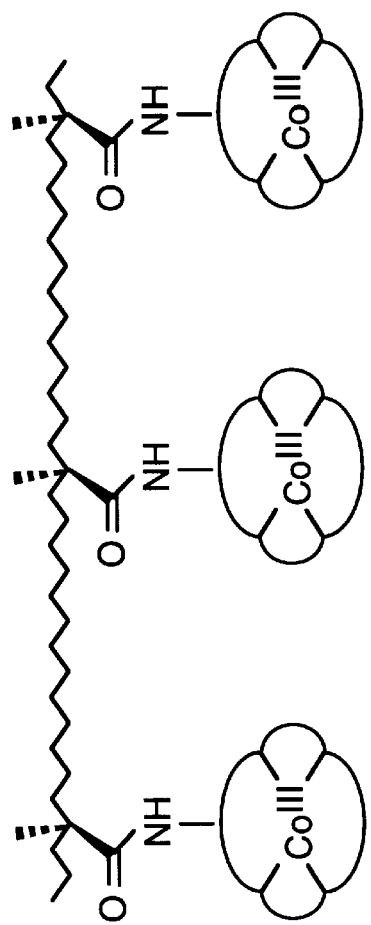
FIG. 3 is a schematic view of an amino pendant macrocyclic metal complex covalently bound to an acrylic polymer.

This may then be copolymerized with a twenty fold excess of various acryloyl monomers to yield an acrylic polymer that contains a macrocyclic cobalt complex as a sidechain approximately every 20 residues, shown schematically in FIG. 3.

Figure 4:
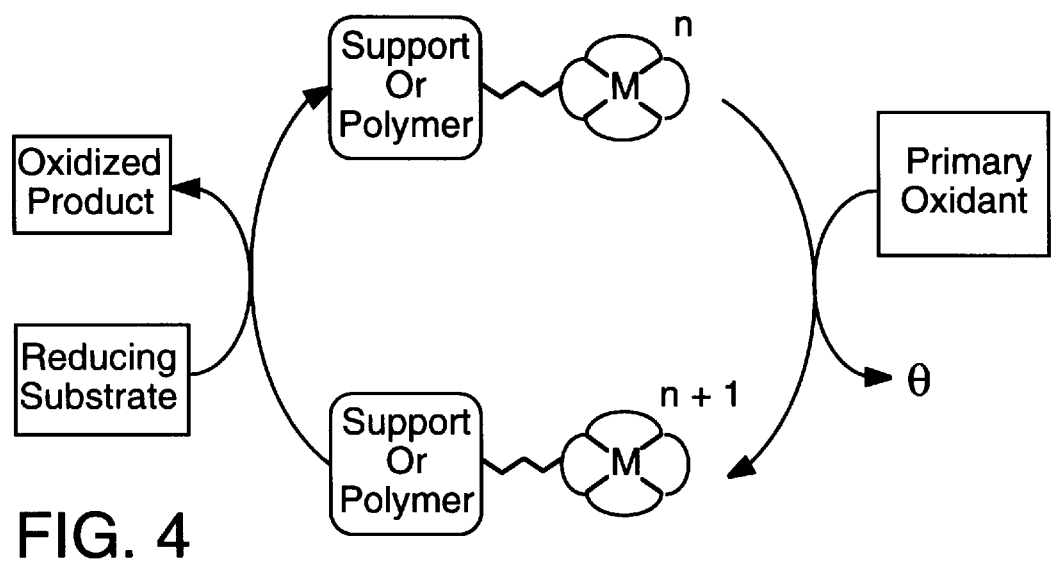
FIG. 4 is a schematic view of a recyclable metallo-oxidant system.

By anchoring the macrocyclic metal complex to a polymer or some other support, the metal may be reclaimed and recycled according to the system shown schematically in FIG. 4. Environmentally toxic metals, for example $Cr^{VI}$ can be replaced by more environmentally benign oxidation reagents, such as $Co^{IV}$ or $Co^{III}L^{I}$ species, where $L^{I}$ refers to a ligand centered oxidation.

Referring to FIG. 4, following the desired oxidation process, the anchored oxidant can be recycled via collection and reoxidation with a primary oxidant, such as hypochlorite, bromine or by electrolysis. Use of anchored macrocyclic metal species is expected to provide a viable method to significantly reduce the levels of discharge of toxic spent metallic species into the environment. The polymer bound oxidant system of FIG. 4 serves as an example of a recyclable "Green" oxidation reagent.

EXPERIMENTAL SECTION

Syntheses of Oxidatively Robust Tetraamido Ligands.

Materials. All solvents and reagents were reagent grade (Aldrich, Aldrich Sure-Seal, Fisher) and were used as received. Microanalyses were performed by Midwest Microlabs, Indianapolis, Ind.

Electrochemical Measurements. Cyclic voltammetry was performed under $N_2$ in a three compartment cell using a glassy carbon disk working electrode (A ~0.0078 $cm^2$ or 0.071 $cm^2$), a Pt wire counter electrode, and a sodium chloride saturated calomel electrode (SSCE) as reference. $CH_2Cl_2$ (Aldrich Sureseal) or $CH_3CN$ (dried over $CaH_2$) were employed as solvents with a supporting electrolyte of [$Bu_4N$][$ClO_4$] (0.1 M, Fluka, vacuum dried 24 h ° C.) or [$Bu_4N$][$PF_6$] (0.1 M, Fluka puriss). A Princeton Applied Research Model 273 Potentiostat/Galvanostat controlled with a Compudyne 486DX computer was used and current/voltage curves were recorded on a Graphtec Model WX1200 X-Y recorder, or using a Princeton Applied Research Model 173/179 potentiostat/digital coulometer equipped with positive feedback IR compensation, a Model 175 universal programmer, and a Houston Instruments Model 2000 X-Y recorder. For some experiments, ferrocene (Fc) was added as an internal potential standard at the conclusion. Formal potentials were calculated as the average of anodic and cathodic peak potentials and are reported vs NHE. Peak-to-peak separation of the $Fc^+$/Fc couple was similar to that of the iron compound couples in all cases. Plots of peak current vs the square root of scan speed over the range 20–500 mV $s^{-1}$ were found to be linear for all couples.

Mass Spectrometry. Electrosptay ionization mass spectra were acquired on a Finnigan-MAT SSQ700 (San Jose, Calif.) mass spectrometer fitted with an Analytica of Branford electrospray interface. Electrospray voltages of 2400–3400 V were utilized. Samples were dissolved in either acetonitrile or dichloromethane at concentrations of approximately 10 pmol/µl and were introduced into the ESI interface prior to data acquisition by direct infusion at a flow rate of 1 µl/min and were introduced prior to data acquisition. Positive ion electron impact ionization (70 ev) MS experiments were performed on a Finnigan-MAT 4615 quadrupole mass spectrometer in conjunction with an INCOS data system. The ion source temperature was 150° C. and the manifold chamber temperature was 100° C. Sample introduction was by means of a gas chromatograph or a direct insertion probe. Positive ion fast atom bombardment mass spectra were acquired on a Finnigan-MAT 212 magnetic sector instrument in combination with an INCOS data system. The accelerating voltage was 3 kV and the ion source temperature was approximately 70° C. An Ion Tech saddle field fast atom gun was employed with xenon at 8 keV. Thioglycerol was utilized as the FAB matrix. Positive ion electron impact ionization (70 eV) MS/MS experiments were performed on a Finnigan-MAT TSQ/700 tandem quadrupole mass spectrometer. Sample introduction was by means of a direct insertion probe. The ion source was maintained at 150° C. and the manifold chamber was held at 70° C. Collision-induced dissociation (CID) was achieved by introducing argon into the center rf-only collision octapole until the pressure in the manifold reached 0.9–2.5×$10^{-6}$ Torr. The nominal ion kinetic energy for CID product ions was <35 eV (laboratory reference). High resolution data were obtained on a JEOL JMS AX-505H double focusing mass spectrometer in the EB configuration using a resolution of 7500. Sample introduction was by means of a gas chromatograph or direct insertion probe. During mass spectral acquisition, perfluorokerosene was introduced into the ion source by means of a heated inlet. Exact mass assignments were obtained by computer-assisted interpolation from the masses of perfluorokerosene. GC/MS conditions: column, 20 m×0.25 mm DB-1701 (J & W Scientific); carrier gas, helium with a linear velocity of 40 cm/sec; injector, 125° C.; column temperature, 35° C. for 3 min, followed by an increase at 10° C./min to 100° C.; injection, split mode, appx. 50:1 ratio.

Spectroscopic Methods. 300 MHz $^1$H NMR spectra and 75 MHz $^{13}$C NMR spectra were obtained on an IBM AF300 instrument using an Oxford Superconducting magnet system, data acquisition was controlled by Bruker software. Infrared spectra were obtained on a Mattson Galaxy Series 5000 FTIR spectrometer controlled by a Macintosh II computer. UV/vis spectra were obtained on a Hewlett Packard 8452A spectrophotometer driven by a Zenith Z-425/SX computer. Conventional X-Band EPR spectra were recorded on a Bruker ER300 spectrometer equipped with an Oxford ESR-900 helium flow cryostat. Mössbauer spectra were obtained on constant acceleration instruments and isomeric shifts are reported relative to an iron metal standard at 298 K. In order to avoid orientation of polycrystalline samples by the applied magnetic field, the samples were suspended in frozen nujol.

Syntheses of Diamines not Readily Available Commercially

Example 1

A. 1,2-Diamino-4,5-Dimethoxy Benzene from 1,2-Dimethoxy Benzene (veratrole)

1,2-Dinitro-4,5-Dimethoxy Benzene: Veratrole was doubly nitrated according to the procedure of Drake et al, in "Synthetic Antimalarials. Some Derivatives of 8-Aminoquinoline", J. Amer. Chem. Soc., 1536, Vol. 68 (1946). Nitric acid (68.3 g, conc.) was added (dropwise, 1 h) to a well stirred solution of veratrole (48.3 g, 350 mmol, d=1.084) in glacial acetic acid (1450 mL) initially cooled to 15° C. The mixture needs to be held below 40° C. but above 10° C. by cooling and proper regulation of the rate of addition of the acid. Considerable mononitroveratrole separated out. Stirring was continued and additional nitric acid (212.7 mL, fuming) was added (dropwise, 1 h) while the temperature of the solution was held below 30° C. As the second nitration proceeded the mono nitroveratrole dissolved and when all the acid had been added, the solution was clear. The nitration mixture was allowed to stand for two hours and was then poured into ca. 1.5 L of ice/cold water. The precipitated dinitro compound was filtered, washed copiously with water until free from acid (pH>5), and recrystallized directly from a minimum of hot EtOH (600 mL). The yield of 1,2-Dimethoxy-4,5-dinitrobenzene was 69.0 g (87%). Characterization: m.p. 129.5–130.5° C. $^1$H NMR (CDCl$_3$) δ [ppm]: 7.35 (s, 2H, ArH), 4.02 (s, 6H, OCH3). IR nujol ν[cm$^{-1}$]: 3124 (s, w, Aryl CH), 3073 (s, w, Aryl CH), 1592 (s, str, Aryl ring stretch), 1535 & 1518 (s, str, ArNO$_2$). Anal. Calcd. For $C_8H_8N_2O_6$: C, 42.11; H, 3.53; N, 12.28. Found: C, 42.12; H, 3.54; N 12.33.

1,2-Diamino-4,5-Dimethoxy Benzene: 1,2-Dimethoxy-4,5-dinitrobenzene (10 g, 43.8 mmol) was reduced to 1,2-Dimethoxy-4,5-diamino benzene in acidic MeOH (175 mL+2 eq. of mineral acid, (i.e., 10 mL of conc. HBr)) by catalytic hydrogenation using 10% Pd/C catalyst (24–36 h, 20–22 psi of H$_2$ was consumed from the reservoir). If more than 2 eq. of HBr are added initially the Pd/C catalyst is found to be strongly inhibited. After hydrogenation was complete an additional 4–5 eq. of conc. mineral acid was added to protect the material from aerial oxidation and the mixture rotary evaporated to yield a red/purple oil. The crude material was purified by adding a small volume of Abs. EtOH, then pouring the slurry into a 600 mL volume of ice cold Et$_2$O, with storage in the freezer overnight. The red-purple product was collected by filtration, air dried briefly then stored in a dessicator to complete the drying process. Prolonged exposure of the diamine salt to air/water causes a green color to develop which appears indicative of irreversible oxidation. Hydrogenation yield was ≈90%. Characterization of the red-purple 1,2-Dimethoxy-4,5-Diaminobenzene (dihydrobromide salt hydrate). $^1$H NMR (d$^5$ pyridine) δ [ppm]: 10.35 (s, br, 7.5 H, H$_2$O/py.HBr/R—NH$_2$ rapidly exchanging), 7.35 (s, 2 H, ArH), 3.60 (s, 6 H, ArOCH$_3$). IR (nujol/NaCl) ν [cm$^{-1}$]: 3085 (br, OH), 2557 (s, str, ArNH$_3^+$), 1623 (s, w, asymmetric NH$_3^+$ bend/Aryl ring stretch), 1539, 1519 (s, m. symmetric NH$_3^+$ bend). (Anal. Calcd. for $C_8H_{12}N_2O_2$) (HBr)$_2$ (H$_2$O)$_{0.66}$: C, 28.09; H, 4.52; N, 8.19. Found: C, 27.82; H, 4.18; N, 8.37. Independent confirmation of hydration was obtained from IR and NMR spectroscopy.

Preparation of the anhydrous sulfate salt of 1,2-Diamino-4,5-Dimethoxy Benzene has been reported by Nakamura, M. et. al. in "Fluorimetric Determination of Aromatic Aldehydes with 4,5-Dimethoxy-1,2-Diaminobenzene" Anal. Chim. Acta. (1982), 134, p.39–45 as follows: 1,2-Diamino-4,5-Dimethoxybenzene (2 g) was dissolved in EtOH (20 mL) and mixed with H$_2$SO$_4$ (conc., ca. 2 mL). The product was recrystallized from EtOH to almost colorless needles (yield ca. 2 g). Anal. Calcd for $C_8H_{14}O_6N_2S$: C, 36.1; H, 5.3; N, 10.5. Found: C, 35.85; H, 5.6; N, 10.4.

B. 1,2-Diamino-4-acetamidobenzene from 1,4-diamino-2-nitrobenzene (2-Nitro-1,4-phenylenediamine)

1-Amino-2-nitro-4-acetamidobenzene: 1,4-diamino-2-nitrobenzene (2-nitro-1,4-phenylenediamine) was selectively acetylated according to the method of McFarlane et. al, J. Chem. Soc. Perkin Trans., 691 (1988). The amine meta to the nitro group is readily acetylated using acetic anhydride in acetone (the amine ortho to the nitro group is strongly deactivated). The yield of 1-Amino-2-nitro-4-acetamidobenzene (2-nitro-4-acetamido aniline) was >90%. Characterization: $^1$H NMR (CD$_3$OD) δ [ppm]: 8.3 (m, 1 H, ArH), 7.5 (M, 1 H, ArH), 6.9 (M, 1 H, ArH), 2.1 (s, 3 H, acetyl CH3) in good agreement with McFarlane. IR (nujol/NaCl) ν [cm$^{-1}$]: 3470 (s, str, HOAc), 3340–3150 (m, m/str, acetamide ArNH+ArNH$_2$), 1661 (s, str, acetamide CO), 1643 (s, str, H bonded acetamide CO), 1592 (s, m/w, aryl stretch), 1547 (s, str, ArNO$_2$) & 1512 (s, m ArNO$_2$). Anal. (Dried at 80° C.) Calcd for $C_8H_9N_3O_3$: C, 49.23; H, 4.65; N, 21.53. Found: C, 49.36; H, 4.55; N, 21.31.

1,2-Diamino-4-acetamidobenzene: 1-Amino-2-nitro-4-acetamidobenzene was reduced to 1,2-Diamino-4-acetamidobenzene in acetic acid (HOAc)/MeOH using catalytic hydrogenation over a 10% Pd/C catalyst. The material was isolated as the dihydrochloride salt. Yield >90%. Characterization: $^1$H NMR (CD$_3$OD) δ [ppm]: 6.94 (m, 1 H, ArH), 6.68 (m, 1 H, ArH), 6.62 (m, 1 H, ArH), 2.1 (s, 3 H, acetyl CH$_3$). IR (nujol/NaCl) ν [cm$^{-1}$]: 3348 (s, str, acetamide ArNH), 3226–3100 (m, m, ArNH$_2$), 2588 (s, br, str, ArNH$_3^+$), 1649 (s, str, acetamide CO), 1623 (s, str, H bonded acetamide CO). Anal. (Dried at 80° C.) Calcd for $C_8H_{13}N_3OCl_2$ (HCl/H$_2$O)$_{0.1}$: C, 39.45; H, 5.50; N, 17.25; Cl, 30.57. Found: C, 39.39; H, 5.53; N, 17.32; Cl, 30.37. Presence of solvate HCl/H$_2$O was confirmed by IR, and is consistent with the constant boiling 36.5–38% HCl used to generate the hydrochloride salt.

C. 2,4-Diamino-2,4-Dimethyl Pentanone from 2,4-dimethylpentanone 2,4-Dibromo-2,4-dimethylpentanone: To 2,4-dimethylpentanone (85 mL, 68.5 g, 0.60 mol) in CCl$_4$ or 1,2 Dichloroethane (1 L) was added N-bromo-succinimide (NBS, 240 g, 1.35 mol, 2.26 equiv). The mixture was heated under reflux, and benzoyl peroxide (ca 20 mg) was added to the refluxing mixture. While the solution was heated under reflux (24 h), a pale orange solid (succinimide) floated to the surface of the halogenated solvent, while unreacted NBS remained at the bottom. Benzoyl peroxide was repeatedly added to the refluxing mixture (ca 20 mg; 12–24 hr intervals) until no NBS was visible, usually the reaction was complete after 24 hours. When the reaction was complete, the solids were collected by filtration and discarded, the halogenated solvent/$Br_2$ was removed from the mother liquor under reduced pressure, leaving a pale yellow oil. To remove residual halogenated solvent, 95% EtOH (100 mL) was added, solvents were again removed under reduced pressure, and a yellow slightly impure oil resulted (159.99 g, 0.59 mol, 98%). $^1$H NMR ($CDCl_3$): 2.1 (s). IR (neat/NaCl) ν [$cm^{-1}$]: 3375 (s, w, impurity OH), 3014, 2978, 2933 (s, str, CH), 2858 (s, w, CH), 1701 (s, str, ketone CO).

2,4-Diazido-2,4-dimethylpentanone: A solution of 2,4-Dibromo-2,4-dimethylpentanone prepared as above or purchased from Lancaster Synthesis (89.8 g, 0.33 mol) in EtOH (1.2 L, 95%) was added to a solution of $NaN_3$ (Caution., 47.2 g, 0.726 mol, 2.2 equiv) in water (0.6 L). The solution was heated under reflux (16 h) to give a pale orange solution. The EtOH was removed under reduced pressure until the solution became cloudy. The cloudy aqueous solution was extracted, still warm, with pentane (500 mL) three times, and the combined extracts were dried over $Na_2SO_4$ and concentrated to 300 mL under reduced pressure. Glacial acetic acid (100 mL) was then added, and the remaining pentane was removed under reduced pressure. This workup was required to remove any excess $NaN_3$ since the product is exposed to Pd/C in the next step, and care should be taken to avoid the formation of heavy metal azides (due to the risk of explosion). The solvent was removed from a small sample under reduced pressure to give a neat oil (<20 mg) for spectroscopic characterization: $^1$H NMR ($CDCl_3$): 1.54 (s). IR (neat) ν [$cm^{-1}$]: 2115 ($RN_3$), 1720 (ketone CO). It should be noted, for safety, that the organic azides produced in this and related azide based syntheses are never isolated in concentrated forms or as solids in quantities greater than 20 mg.

2,4-Diamino-2,4-dimethylpentan-3-one: Glacial acetic acid (50 mL) was added to the HOAc solution of the dialkyl azide formed in the previous step, and this solution was added to 10% Pd/C (2.7 g). The mixture was hydrogenated at 50 psi (1 week) in a Parr hydrogenator. Because the reaction evolves one $N_2$ molecule for every $H_2$ molecule absorbed, the bomb was evacuated and repressurized 10 times with $H_2$ to 50 psi. ($H_2$ from the high pressure reservoir is not efficiently consumed.) The charcoal was removed by filtration, and HOAc was removed under reduced pressure. After HBr was added (48%, 76 mL), the mixture was dissolved in EtOH. The volatiles were removed under reduced pressure to yield a tan solid, which was washed with a mixture (200 mL) of THF (50%), EtOH (45%), and conc. HBr (5%) or with a mixture of THF (95%) and conc. HBr (5%). The resulting white powdery product was the dihydrobromide salt of 2,4-Diamino-2,4-dimethylpentan-3-one (56.2 g, 48% from 2,4-Dibromo-2,4-dimethylpentanone). Additional product may be collected from washings that have been pooled from several different preparations. The product must be stored as the dihydrobromide or dihydrochloride salt to protect the amines from oxidative degradation. Characterization: $^1$H NMR ($CDCl_3$/DMSO-$d^6$) of 2,4-diamino-2,4-dimethyl-pentan-3-one. 2 HBr: 8.62 (6H, s, br, $NH_3$), 1.77 (12 H, s, Me). IR (free base, nujol mull) ν [$cm^{-1}$]: 3460–3160 ($RNH_2$), 1690 (ketone CO). Anal. (Dried at 80° C.) Calcd for $C_7H_{16}N_2O$. $(HBr)_2$: C, 27.47; H, 5.93; N, 9.15; Br, 52.22. Found: C, 27.43; H, 5.91; N, 9.11; Br, 52.46.

Syntheses of Macrocyclic Tetraamido-N Donors Ligands

Example 2

Macro Linker Intermediate (A-L-A) synthesis, from α-methyl alanine and diethyl malonyl dichloride (a Tetramethyl Diethyl substituted intermediate).

A two-neck flask (1 L) fitted with a pressure equalizing addition funnel (250 mL) and a septum is placed under $N_2$. α-amino isobutyric acid (i.e. α-methyl alanine) (20.62 g, 0.2 mol) and dry pyridine (250 mL, dryed over 4 Å mol sieves) are added to the flask and heated 60–70° C. with stirring, then diethyl malonyl dichloride (23.23 mL, 0.135 mol) dissolved in dry pyridine (100 mL, dryed over 4 Å mol sieves) is added to the addition funnel. The contents of the addition funnel are added (dropwise, 1 h) to the reaction and the acylation allowed to proceed (60–70° C., 30–36 h) under $N_2$ or with a drying tube fitted. Once the acylation is complete the reaction is quenched by adding $H_2O$ (30 mL) and stirring (60–70° C., 24 hrs). The solvent volume is reduced on the rotary evaporator to give an oil, then HCl (conc., ca. 25 mL) is added to a final pH of 2–3. The hot solution is set in the refrigerator (4° C., 15 h), and the resulting tan product collected by frit filtration, and washed thoroughly with acetonitrile (2×100 mL). The air-dried white product, (16.5–19.8 g, 50–60% yield) should be stored in a dessicator. This product is usually pure enough for ring closure reactions, but recrystallization may occasionally be required. Characterization: $^1$H NMR spectrum ($d^5$-pyridine) δ [ppm]: 8.9 (s, 2H, NH amide); 2.2 (q, 4H) 1.8 (s, 12H); 1.2 (t, 6H). IR(Nujol mull): ν [$cm^{-1}$]=3310 (amide NH); 1721 (carboxylic CO), 1623 (amide CO). Anal. Calcd for $C_{15}H_{21}N_2O_6$: C, 54.53; H, 7.93; N, 8.48. Found: C, 54.48; H, 7.88; N, 8.47.

Example 3

Large Scale, Macro Linker Intermediate (A-L-A) synthesis, from α-methyl alanine and diethyl malonyl dichloride (a TMDE substituted intermediate).

A two-neck flask (2 L, RB+Claisen) fitted with a pressure equalizing addition funnel (250 mL) and septa, is placed under $N_2$. α-aminoisobutyric acid (i.e. α-methyl alanine) (90.3 g, 0.9 mol) is added, anhydrous pyridine (1.4 L, sure seal) is cannulated into the flask and the reaction mix heated to 45–55° C. and stirred. Pyridine (100 mL, sure seal) and then diethyl malonyl dichloride (104.4 mL, 0.61 mol) are cannulated into the addition funnel. The contents of the addition funnel are added (dropwise, 3–4 h) to the reaction, the addition funnel is then removed, and the acylation allowed to proceed (55–65° C., 120–130 h) under $N_2$. Once the acylation is complete the reaction is quenched by adding $H_2O$ (100 mL) and stirring (60–70° C., 24–36 hrs). The solvent volume is reduced on the rotary evaporator to give an oil, then HCl (conc., ca. 110 mL) is added to a final pH of 2–3. The hot solution is set in the refrigerator (4° C., 15 h), and the resulting tan product collected by frit filtration, and washed thoroughly with acetonitrile (700 mL, 150 mL) by stirring in an erlenmeyer flask. The air-dried white product (87.9 g, 60% yield), is crushed in a mortar and pestle and stored in a dessicator. The large scale reaction amide intermediate product is more likely to need recrystallization before use in ring closure reactions.

Example 4

Recrystallization of the TMDE substituted intermediate from above Crude TMDE intermediate from Example 3 (50.4 g, 0.153 mol) is dissolved in $H_2O$ (500 mL, deionized) by adding $Na_2CO_3$ (16.2 g, 0.153 mol) in three aliquots slowly and carefully to avoid excessive frothing, with good stirring and mild heating. The solution is brought to a boil, filtered and acidified with HCl (conc., 30 mL, 0.36 mol). The solution is allowed to cool (overnight, 4° C.) and the white precipitate filtered off and washed with acetonitrile (250 mL). The air dryed product (38.8–45.4 g, recryst. yield 77–90%) should be stored in a dessicator.

Example 5
Hexa Methyl (HM) Intermediate (A-L-A)

The synthesis of the HM intermediate is identical to that for the TMDE intermediate in Example 2 with the following exceptions, dimethyl malonyl dichloride (17.8 mL, 0.135 mol) is substituted for diethyl malonyl dichloride, and the reaction temperature must be decreased to 55–65° C. due to the lower boiling point of the acylating agent. The yield of hexamethyl intermediate is 45–60%. Characterization: $^1$H NMR (d$^5$ pyridine, δ [ppm]); 9/2–9.8 br s, 2 H (carboxylic OH), 8.23 s, 2 H (amide), 1.87 s 12 H (CH$_3$), 1.74 s 6 H (CH$_3$). IR (nujol/NaCl) ν [cm$^{-1}$]: 3317.0 (amide NH); 1717.9 (carboxylic CO); 1625.7 (amide CO). Anal. (dried at 100° C.) Calcd. for C$_{13}$H$_{22}$N$_2$O$_6$; C 51.63, H 7.34, N 9.27. Found; C 51.64, H 7.35, N 9.33.

Example 6
Recrystallization of HM Intermediate

Crude hexamethyl (HM) intermediate was recrystallized in the same manner as the TMDE amide intermediate. Due to the slightly higher water solubility of the HM amide intermediate a little less H$_2$O should be employed.

Example 7
Di CyHex Di Ethyl Intermediate

A round bottom flask (500 mL), is charged with 1-amino-1-cyclohexane carboxylic acid (15 g, 0.1 mol), then fitted with a pressure equalizing addition funnel (40 mL), capped with a septum, and purged with nitrogen. Anhydrous pyridine (300 mL) is cannulated into the reaction flask through the addition funnel, and 20 mL into the addition funnel. Start heating the system and stabilize the temperature at 60° C. Once 60° C. is reached, one-third of the total diethyl malonyl dichloride to be utilized in the reaction (i.e. 6 mL, 0.033 mol) is added via syringe to the addition flask. The mixture of pyridine/diethyl malonyl dichloride is added dropwise to the reaction and the acylation allowed to proceed for 12 hours. A second (6 mL, 0.033 mol) and third aliquot (6 mL, 0.033 mol) are added at 12 hour intervals. After all of the acylating agent has been added and allowed to react (total reaction time 48–56 h), 20 mL of water is added dropwise to the reaction. The reaction is heated for an additional 24 hours to ring open the mono and bis oxazalone intermediates and yield the diamide dicarboxylic acid. Removal of the pyridine by rotary evaporation yields a pale yellowish tan sludge which is acidified to pH 2 with HCl (conc.). The crude product is collected by filtration, washed with acetonitrile and air dried to yield the white DiCyHexDE-amide intermediate (16 g, 74%). Characterization: $^1$H NMR (d$^5$-pyridine) δ [ppm]: 8.30 (s, 2H, NH amide), 2.60 (m, 4 H, cyhex), 2.25 (q, 4 H, ethyl CH$_2$), 2.15 (m, 4 H, cyhex), 1.8–1.5 (m, 10 H, cyhex), 1.25 (m, 2 H, cyhex), 1.20 (t, 6 H, ethyl CH$_3$). $^{13}$C NMR broadband decoupled (d$^5$-pyridine) δ [ppm]: 178.0, (carboxylic CO), 174.3 (amide CO), 60.5 (cyhex quat), 59.4 (malonyl quat), 33.0 (cyhex α CH2), 30.3 (ethyl CH$_2$), 26.0 (cyhex γ CH$_2$), 22.3 (cyhex β CH$_2$), 9.9 (ethyl CH$_3$). IR (nujol/NaCl) ν [cm$^{-1}$]: 3307 (amide NH); 3150 (sh, br, m, amide NH/carboxylic OH), 3057 (s, str, H bonded amide NH/carboxylic OH), 1717 (s, str, carboxylic CO); 1621 (s, str, amide CO). Anal. Calcd for C$_{21}$H$_{34}$N$_2$O$_6$: C, 61.44; H, 8.35; N, 6.82. Found: C, 61.41; H, 8.38; N, 6.90%.

Example 8
Di CyHex Diethyl Mono Oxazalone

Failure to quench the Di CyHex Di Ethyl Intermediate Reaction (with heat & water, see above) at a stoichiometry of 1.35 diethyl malonyl dichloride: 2 Cy Hex amino acid, leads to a mixture of the DiCyHexDE-amide intermediate and mono oxazalone products. The DiCyHexDE Mono Oxazalone product is moderately soluble in boiling cyclohexane while the cyclohexyl amide intermediate is not, allowing for a simple separation of the product mixture. ca. 10 g of mixed amide intermediate and mono oxazalone containing some residual CH$_2$Cl$_2$ was boiled with vigorous stirring in 400–500 mL cyclohexane. The insoluble DiCyHexDE-amide intermediate product was collected by hot gravity filtration while the mono oxazalone product crystallized out gradually as the cyclohexane solution cooled & evaporated. Yield amide intermediate ca. 6 g, yield mono oxazalone ca. 4 g. Characterization of the mono oxazalone: $^1$H NMR (d$^5$-pyridine) δ [ppm]: 9.7 (s, 1H, amide NH), 2.7–1.6 (unresolved Cy Hex groups), 1.05 (t, 6 H, ethyl CH$_3$). IR (nujol/NaCl) ν [cm–1]: 3309 (sh, w, amide NH); 3229 (s, str, H bonded amide NH/carboxylic OH), 3166 (s, str, H bonded amide NH/carboxylic OH), 3083 (s, str, H bonded amide NH/carboxylic OH), 1834 (s, str, oxaz C=O), 1809 (s, m, H bonded oxaz C=O), 1743 (s, str, carboxylic CO), 1663 (s, str, oxaz C=N), 1639 (s, br, str, amide CO). Anal. Calcd for C$_{21}$H$_{32}$N$_2$O$_5$ (C$_6$H$_{12}$) 0.25: C, 65.35; H, 8.53; N, 6.77. Found: C, 65.07; H, 8.67; N, 6.68%. Presence of solvate cyclohexane was confirmed by $^{13}$C NMR.

Macrocyclization Reactions

Examples of several synthetic routes for the preparation of macrocyclic tetraamido ligands follow.

Phosphorus Trichloride Coupling

Phosphorus trichloride coupling of the amide-containing intermediate (A-L-A) to aromatic 1,2-diamines yields macrocyclic tetraamides safely, cheaply and in high yield. Two distinct variations of the PCl$_3$ coupling method are useful, the differences relate to the order of addition and choice of reagents utilized. These methods are applicable to the preparation of a wide variety of different macrocycles with different electronic substituents present on the bridge diamine, or steric substituents present on the amide intermediate, primarily because of the parallel incorporation of the macro linker type of amide intermediates into all of the syntheses.

Example 9
A. Macrocycle Synthesis via PCl$_3$ Coupling

A long neck flask (250 mL) is charged with the amide intermediate of Examples 2–8, (10 mmol) a stir bar and then baked in the oven (80–100° C., 30–45 mins). The hot flask is placed under N$_2$, aryl diamine (10 mmol) is added and anhydrous pyridine (50 mL, sure seal) cannulated in. The flask is heated (50–60° C.) and PCl$_3$ (d=1.574 g/mL, 1.72 mL, 20 mmol) syringed in as quickly as possible without excessive refluxing. This is an exothermic reaction, so caution should be used. The temperature is then increased to reflux or just below reflux (100–115° C.) and the reaction allowed to proceed under N$_2$ (48 h). After the acylation is complete, the contents of the flask are acidified with HCl (1 eq., ca. 60 mL) to a final pH ≈2. The mixture is transferred to an erlenmeyer (water is used to rinse the flask) and stirred with CH$_2$Cl$_2$ (300 mL, 2–3 h), then extracted with additional CH$_2$Cl$_2$ (2×150 mL). The combined organic layers are washed with dilute HCl (0.1 M, 2×100 mL) followed by dilute aqueous Na$_2$CO$_3$ (2×5 g /100 mL). The organic solvents are removed on the rotary evaporator to yield crude product (30%). The weight of crude product is usually equivalent to the initial weight of diamine.

B. Macrocycle Synthesis via PCl$_3$ Coupling

A long neck flask (250 mL) is charged with MgSO$_4$ (5 g), a stir bar, aryl diamine (10 mmol) and pyridine (50 mL, dryed over 4 Å mol sieves) then placed under $N_2$. $PCl_3$ (d=1.754 g/mL, 1.72 mL, 20 mmol) is added via syringe and the mixture brought to reflux for 30 mins, an orange/yellow precipitate forms. The mixture is cooled somewhat, an amide intermediate (10 mmol) is added, then the mixture is refluxed under $N_2$ (115° C., 48 h). After the acylation is complete, the contents of the flask are acidified with HCl (1 eq., ca. 60 mL) to a final pH ≈2. The mixture is transferred to an erlenmeyer and stirred with $CH_2Cl_2$ (300 mL, 2–3 h), then extracted with additional $CH_2Cl_2$ (2×150 mL). The combined organic layers are washed with dilute HCl (0.1 M, 2×100 mL) followed by dilute $Na_2CO_3$ (2×5 g/100 mL). The organic solvents are removed on the rotary evaporator to yield crude product (30%). The weight of crude product is usually equivalent to the initial weight of diamine.

Note: For larger scale macrocyclization reactions, the ring closure times are increased to 4–5 days at reflux, and most of the pyridine present at the end of the reaction is removed via rotary evaporation prior to acidification.

Example 10
TMDE-DCB from TMDE Intermediate+DCB Diamine 1,2-Diamino-4,5-dichlorobenzene (1.77 g, 10 mmol) was utilized as the aryl diamine with TMDE amide intermediate (3.3 g, 10 mmol) in the $PCl_3$ method A or B macrocyclization reaction. The crude macrocyclic product (2.7 g) was recrystallized from a minimum amount of hot 95% EtOH by evaporation to yield pure TMDE-DCB (1.5 g, 32%). Characterization: $^1H$ NMR ($CD_2Cl_2$) δ [ppm]:7.65 (s, 1 H, ArH), 7.35 (s, 2 H, amide NH), 6.45 (s, 2H, amide NH), 1.90 (q, 4 H, ethyl $CH_2$), 1.57 (s, 12 H, $RCH_3$), 0.85 (t, 6H, ethyl $CH_3$). IR (nujol/NaCl) ν [$cm^{-1}$]: 3454 (trace ROH), 3346 (br, amide NH), 1706&1688&1645 (amide CO). Anal.Calcd. for $C_{21}H_{28}Cl_2N_4O_4$; C, 53.51; H, 5.99; N, 11.89. Found C, 53.58; H, 6.09; N, 11.89.

Example 11
TMDE-B from TMDE Intermediate+B Diamine
1,2-Diaminobenzene (i.e. o-phenylene diamine) (1.08 g, 10 mmol) was utilized as the aryl diamine with the TMDE amide intermediate (3.3 g, 10 mmol) in the $PCl_3$ method A or B macrocyclization reaction. The crude macrocyclic product (1.5 g) was recrystallized from a minimum amount of hot 95% EtOH by evaporation to yield pure TMDE-B (≈25% from diamine). Characterization: $^1H$ NMR ($CDCl_3$) δ [ppm]: 7.55 (m, 2 H, ArH), 7.48 (s, br, 2 H, aryl amide NH), 7.17 (m, 2 H, ArH), 6.46 (s, br, 2 H, alkyl amide NH), 2.07 (m, br, 4 H, ethyl $CH_2$), 1.60 (s, 12 H, $RCH_3$), 0.89 (t, 6 H, ethyl $CH_3$. IR (nujol/NaCl) ν [$cm^{-1}$]: 3395&3363 (amide NH), 1702&1680&1652&1635 (amide CO). Anal. Calcd. for $C_{21}H_{30}N_4O_4 \cdot H_2O$: C, 59.98; H, 7.67; N, 13.32. Found: C, 60.18; H, 7.20; N, 13.18.

Example 12
TMDE-DMB from TMDE Intermediate+DMB Diamine
1,2-Diamino-4,5-Dimethylbenzene (1.36 g, 10 mmol) was utilized as the aryl diamine with Tetramethyl Diethyl amide intermediate (3.3 g, 10 mmol) in the $PCl_3$ method A or B macrocyclization reaction. The crude macrocyclic product (1.6 g) was recrystallized from a minimum amount of hot 95% EtOH by evaporation to yield pure TMDE-DMB (≈25% from diamine). Characterization: $^1H$ NMR (DMSO $d^6$) δ [ppm]: 8.00 (s, 2 H, amide NH), 7.67 (s, 2 H, amide NH), 7.28 (s, 2 H, ArH), 2.17 (s, 6 H, aryl $CH_3$), 1.99 (q, 4 H, ethyl $CH_2$), 1.46 (s, 12 H, $RCH_3$), 0.75 (t, 6 H, ethyl CH3). IR (nujol/NaCl) ν [$cm^{-1}$]: 3446 (s, m, trace ROH), 3362 (s, str, amide NH), 3348 (sh, m, amide NH), 3332 (s, str, H amide NH), 1696 (amide CO), 1679 (amide CO), 1651 (amide CO), 1641 (amide CO), 1584 (s, m/w, aryl ring/amide). Anal. Calcd. for $C_{23}H_{34}N_4O_4$: C, 64.16; H, 7.96; N, 13.01, Found: C, 64.09, 64.28; H, 8.04, 7.92; N, 12.86, 13.04.

Example 13
TMDE-DMOB from TMDE Amide Intermediate+DMOB Diamine
1,2-Diamino-4,5-Dimethoxybenzene.2 HBr (5.0 g, 15 mmol) prepared as above was utilized as the aryl diamine directly with the Tetramethyl Diethyl amide intermediate (5.0 g, 15 mmol) in a 1.5 scale $PCl_3$ method A or B macrocyclization reaction. The crude macrocyclic product (3.57 g) was recrystallized from a minimum amount of hot 80–85% EtOH (≈1 g/40 mL) by evaporation to yield pure TMDE-DMOB (≈30% from diamine). Characterization: $^1H$ NMR ($CD_2Cl_2$) δ [ppm]: 7.26 (s, 2 H, amide NH), 7.01 (s, 2 H, ArH), 6.41 (s, 2 H, amide NH), 3.80 (s, 6 H, aryl $OCH_3$, 2.07 (q, br, 4 H, ethyl $CH_2$, 1.54 (s, 12 H, $RCH_3$), 0.90 (t, 6 H, ethyl $CH_3$). IR (nujol/NaCl) ν [$cm^{-1}$]: 3451 (s, m, H bonded $H_2O$), 3391&3347 (amide NH), 1695&1670&1655 (amide CO). Anal . Calcd. for $C_{23}H_{34}N_4O_6$, $(H_2O)_{0.33}$: C, 58.96; H, 7.46; N, 11.96, Found (ESU); C, 58.90; H, 7.26; N, 11.76. Presence of solvate $H_2O$ was confirmed by $^1H$ NMR and IR.

Example 14
TMDE-Nap from TMDE Intermediate+Nap Diamine
4,5 Diamino Naphthalene (1.68 g, 10 mmol) was utilized as the aryl diamine with the Tetramethyl Diethyl amide intermediate (3.3 g, 10 mmol) in the $PCl_3$ method A or B macrocyclization reaction. Unoptimized yield was 15–20% from diamine. $^1H$ NMR ($CDCl_3$) δ [ppm]: 8.05 (s, 2 H, ArH α ring), 7.75 (m, 2 H, ArH β ring), 7.55 (s, 2 H, Ar amide NH), 7.35 (m, 2H, ArH β ring), 6.45 (s, 2 H, alkyl amide NH), 2.15 (m, br, 4 H, ethyl $CH_2$), 1.65 (s, 12 H, $RCH_3$), 0.90 (t, 6 H, ethyl $CH_3$.

Example 15
HM-DCB from HM Intermediate+DCB Diamine
1,2-Diamino-4,5-Dichlorobenzene (1.77 g, 10 mmol) was utilized as the diamine with Hexa Methyl amide intermediate (3.02 g, 10 mmol) in the $PCl_3$ method A or B macrocyclization reaction. The crude macrocycle (1.33 g, 30%) was recrystallized from a minimum of hot n-propanol by evaporation, 1st crop recrystallization yield was 60%. Characterization: $^1H$ NMR δ [ppm]: 7.69 (s, 2 H, ArH), 7.39 (s, 2 H, amide NH), 6.44 (s, 2 H, amide NH), 1.58 (s, 12 H, arm methyls), 1.53 (s, 6 H, malonate methyls), small n-propanol peaks were noted. IR (nujol/NaCl) ν [$cm^{-1}$]: 3503 (s, br, m-w, n-propanol OH, 3381 (sh, m, amide NH), 3338 (s, str, amide NH), 1689 (s, str, amide CO), 1643 (s, str, amide CO). Anal. Calcd. for $C_{19}H_{24}N_4O_4Cl_2 \cdot (C_3H_8O)_{0.2}$: C, 51.70; H, 5.57, N 12.30% Found C, 51.69; H, 5.63; N, 12.33%.

Example 16
HM-DMOB and HM-B from HM Intermediate+DMOB or B Diamine
The HM intermediate has also been used to synthesize HM-B and HM-DMOB according to the same method and with similar results to those obtained in example 15 for the dichloro derivative. $^1H$ NMR data for HM-DMOB in $CDCl_3$ δ [ppm]: 7.65 (s, 2H, amide NH), 7.21 (s, 2 H, aryl CH), 6.72 (s, 2 H, amide NH), 4.00 (s, 6 H, methoxy $CH_3$), 1.76 (s, 12 H, arm methyls), 1.58 (s, 6 H, malonate methyls). $^1H$ NMR data for HM-B in $d^5$ pyridine δ [ppm]: 8.55 (s, 2 H, amide NH), 8.40 (s, 2 H, amide NH), 7.81 (m, 2 H, ArH aa'bb'), 7.10 (m, 2 H, ArH aa'bb'), 1.77 (s, 12 H, arm methyls), 1.73

(s, 6 H, malonate methyls). The amide peaks tend to shift a few tenths of a ppm in the presence of impurity species such as water, acids etc.

Example 17
DiCyHexDE-DCB from DiCyHexDE Intermediate+DCB Diamine 1,2-Diamino-4,5-Dichlorobenzene (1.77 g, 10 mmol) was utilized as the aryl diamine with Di Cy Hex Diethyl amide intermediate (3.3 g, 10 mmol) in the $PCl_3$ method A or B macrocyolization reaction. Due to the increased steric hindrance an increased ring closure reaction time is recommended (3–4 days as opposed to the usual 48 h). Cy Hex Oxazalones formed as a side product during the reaction are not removed by the acid base workup, so it is necessary to triturate/wash the initially isolated $CH_2Cl_2$ soluble product with pentane to remove the oxazalones. Evaporation of the pentane washes allows for recycling of the oxazalones. The crude pentane insoluble product was recrystallized by dissolving in $CH_2Cl_2$ or $CHCl_3$, adding cyclohexane until slightly cloudy and then evaporating in air (1–2 days) to yield the white microcrystalline DiCyHexDE-DCB product, which was collected by filtration (1.38 g, 25% from diamine). Recrystallization from hot neat toluene with evaporation also appears promising. Characterization: $^1$H NMR ($CDCl_3$) δ [ppm]: 7.70 (s, 2 H, ArH), 7.45 (s, 2 H, amide NH), 6.45 (s, 2 H, amide NH), 2.35 (m, br, 4 H, cyhex), 2.00 (m, br, ≈8 H, cyhex/ethyl $CH_2$), 1.70 (m, br, ≈8 H, cyhex), 1.30 (m, br, ≈4 H, cyhex), 0.90 (t, 6 H, ethyl $CH_3$). Anal. (Dryed at 100° C.) Calcd. for $C_{27}H_{36}Cl_2N_4O_4$, $(C_6H_{12})_{0.2}$: C, 59.60; H, 6.81; N, 9.86, Found: C, 59.60; H, 6.77; N, 9.77. Presence of solvent cyclohexane was confirmed by $^1$H and $^{13}$C NMR.

Example 18
DiCyHexDE-B from DiCyHexDE Intermediate+B Diamine 1,2-Diaminobenzene (ortho-phenylene diamine, 1.08 g, 10 mmol) was utilized as the aryl diamine in a preparation analogous to that for DiCyHexDE-DCB, to yield DiCyHexDE-B (1.25 g, 26% from diamine). Characterization: $^1$H NMR ($CD_3CN$) δ [ppm]: 7.62 (s, 2 H, aryl amide NH), 7.51 (m, 2 H, ArH), 7.18 (m, 2 H, ArH), 6.71 (s, 2 H, alkyl amide NH), 2.12 (m, 6H, Cyhex), 1.85 (q&m, ethyl $CH_2$ & cyhex), 1.62 (m, cyhex), 1.37 (m, cyhex), 0.90 (t, 6 H, ethyl $CH_3$), 0.85 (m, cyhex). IR (nujol/NaCl) ν [cm$^{-1}$]: 3570 (s, m, $H_2O$), 3385 (s, str, amide NH), 314 (s, str, amide NH), 3258 (s, m, br, H bonded amide NH), 1694 (s, str, amide CO), 1651 (s, str, amide CO), 1594 (s, m, aryl ring/amide).

Example 19
Di CyHex Diethyl Bis Oxazalone

This product was obtained as a byproduct of the $PCl_3$ macrocyclization reaction of Di CyHex Di Ethyl Amide Intermediate with o-phenylene diamine. The bis oxazalone is not removed by the acid base workup (it is a neutral molecule and very organic soluble). Washing of the crude macrocyclic/oxazalone product with pentane extracts most of the bis oxazalone into the pentane. Air evaporation of the pentane layer yields the pure bis oxazalone as large (1 cm×1 cm×0.5 cm) transparent prisms. Due to the bulky hydrophobic CyHex groups this oxazalone is much more resistant to hydrolysis than the corresponding methyl derivative. Characterization of the bis oxazalone: $^1$H NMR ($CD_3CN$) δ [ppm]: 2.05 (q, 4 H, ethyl $CH_2$), 1.8–1.4 (Unresolved Cy Hex Groups), 0.88 (t, t H, ethyl $CH_3$). $^{13}$C NMR broadband decoupled ($CD_3CN$) δ [ppm]: 181.0 (oxaz C=O), 162.7 (oxaz C=N), 69.0 (oxaz cyhex quat), 49.0 (malonate quat), 34.3 (cyhex α methylenes), 25.5 (cyhex γ methylenes), 24.9 (malonate methylenes), 21.8 (cyhex β methylenes), 8.3 (ethyl $CH_3$). IR (nujol/Nacl) ν [cm$^{-1}$]: 1822 (s, str, br, oxaz C=O), 1662 (s, str, oxaz C=N). Anal. (Dryed at 50° C.) Calcd. for $C_{21}H_{30}N_2O_4$; C, 67.36; H, 8.07; N, 7.48, Found: C, 67.26; H, 8.15; N, 7.64.

Oxazalone Coupling Reactions

Oxazalone coupling of the amide intermediate to aromatic diamines also yields macrocyclic tetraamides safely, cheaply and in high yield, but with less sensitivity to additional functional groups. All of the macrocycles able to be formed via the $PCl_3$ coupling route with the exception of the CyHex substituted macrocycles (too sterically hindered) can also be manufactured via the oxazalone coupling route. In addition the lesser sensitivity to additional functional groups has opened up the preparation of macrocyclic ligands with additional functional groups designed to confer new properties on the resulting metal complexes. Specific examples include the incorporation of reactive groups (such as amine or vinyl groups) attached in a pendant fashion to the aryl ring of the macrocycle allowing for covalent attachment of the preformed macrocycles to some (polymeric) substrate.

Example 20
Macrocycle Synthesis via Oxazalone Method

A long neck flask (250 mL) is charged with amide intermediate (3.3 g, 10 mmol), a stir bar and then baked in the oven (80–100° C., 30–45 mins). The hot flask is fitted with a septum and placed under $N_2$. Anhydrous pyridine (50 mL, sure seal) is cannulated in and heating commenced while trimethyl acetyl chloride (i.e. pivaloyl chloride) (22–24 mmol) is added via syringe. The temperature is increased to reflux or just below reflux (100–115° C.) and the reaction allowed to proceed under $N_2$ (22–26 h) being careful to avoid cross contamination from other reactions on the $N_2$ line. The reaction goes from a clear pale yellow to a yellow-brown color. After oxazalone formation is complete[5], the aryl diamine (8–10 mmol) is added either as a neat solid or via large bore cannula as a slurry in anhydrous pyridine, or dissolved and degassed under $N_2$ in anhydrous (sure seal) pyridine, if head space and solubility constraints can be satisfied. The ring closure reaction is refluxed for a further 48–72 hours (longer times for larger scales) under $N_2$ without cross contamination from other reactions. The mixture will usually turn brownish black. Once the acylation is complete, the reaction is quenched by adding $H_2O$ (30 mL) and stirring at reflux (100° C., 22–26 hrs). The mixture is cooled and transferred to an RB flask (500 mL) using a minimum of $H_2O$ to rinse the long neck flask. The solvent is removed via rotary evaporation to yield the crude product mixture as an oily tan to brownish black solid. It should be noted that, functional groups permitting, the crude product mixture can be taken up in $CH_2Cl_2$ and washed with dilute aqueous HCl and dilute aqueous $Na_2CO_3$. Removal of the organic solvent at reduced pressure then yields the normal macrocyclic product familiar from the $PCl_3$ coupling reactions and suitable for direct recrystallization as detailed previously to yield pure macrocyclic product.

[5]Pumping an aliquot down and redissolving in dry d$^5$ pyridine yielded a dominant species (>80% bis oxazalone after 24 h at reflux) with $^1$H NMR δ [ppm]: 2.10 (q. 4 H, methylene $CH_2$'s), 1.38 (s, 12 H, $RCH_3$), 0.85 (t, 6 H, ethyl $CH_3$'s). Addition of water to the NMR sample regenerated the normal amide intermediate spectrum after about 20 h at RT.

Example 21
TMDE-AcB from TMDE Intermediate+AcB Diamine via oxazalones.

This macrocycle is the protected form of an amino pendant macrocycle which can be attached to a range of different supports through amide formation between the substrate and the pendant amino group. Due to what is speculated to be formation of an unfavorable hydrogen bond, the ring closure reaction requires lengthy reflux times in order to achieve macrocyclization. 1,2-Diamino-4-acetamidobenzene dihydrochloride (9 mmol) was employed as the diamine in an oxazalone ring closure reaction. The macrocyclization time was increased (reflux, 5 days), followed by the normal quenching reaction and acid base workup to yield a mixture of a triamido containing macrocyclic imidazole and the desired tetraamido macrocycle. Further purification was by silica gel chromatography (1"× 4–5") using acetonitrile as the eluant. Alternatively, the crude product can be purified by recrystallization from hot ethanol, chloroform or dichloroethane. Yield 15–20% from diamine. Characterization: $^1$H NMR (CD$_3$CN) δ [ppm]: 8.31 (s, 1 H, aryl acetamide NH), 7.72 (m, 1 H, ArH), 7.55 (s, 1 H, aryl amide NH), 7.44 (s, 1 H, aryl amide NH), 7.30 (m, 2 H, ArH), 6.86 (s, 2 H, alkyl amide NH), 2.05 (q, 4 H, ethyl CH$_2$'s), 2.01 (s, 3 H, acetyl CH$_3$), 1.49 (d, 12 H, RCH$_3$'s), 0.82 (t, 6 H, ethyl CH$_3$'s). IR (nujol/NaCl) ν [cm$^{-1}$]: 3368 (s, m, amide NH), 3319 (s, m, amide NH), 3291 (sh, m, amide NH), 3268 (s, str, amide NH), 1678 (sh, m, amide CO), 1667 (s, str, amide CO), 1656 (s, str, amide CO), 1639 (sh, m, amide CO), 1608 (s, m, aryl ring/amide). Anal. Calcd for C$_{23}$H$_{33}$N$_5$O$_5$. (H$_2$O)$_{1.25}$: C, 57.31 H, 7.42 N, 14.53 Found: C, 57.02; H, 7.15; N, 14.33. Presence of solvate H$_2$O was confirmed by $^1$H NMR and IR.

Example 22

Synthesis of a peralkylated macrocycle (MAC*), or TMDE-DMP from the TMDE intermediate+2,4-Diamino-2,4-dimethyl-Pentan-3-one (DMP) via the Oxazalone Route.

The PCl$_3$ route to H$_4$[MAC*] (TMDE-DMP) fails to produce appreciable amounts of macrocycle due to what is speculated to be unfavorable complex formation between the diamine ketone functionality and the phosphorus reagent. Unlike the PCl$_3$ route, which is heterogeneous, the oxazalone route to H$_4$[MAC*] is a homogeneous solution method which simplifies the application of diagnostic techniques such as $^1$H NMR to diagnose causes of synthetic failure. Reaction of TMDE bis oxazalone with DMP diamine in dry pyridine fails to form any amides (by NMR analysis). Since the oxazalone route is insensitive to ketone functionalities, the failure to form amides was attributed to acid salt formation of the alkyl amine functionality, the alkyl diamine is 3–4 pK$_a$ units more basic than pyridine while aryl diamines have pK$_a$'s close to that of pyridine. Therefore, a more basic high boiling solvent (triethylamine, tripropylamine, diethylaniline) may be used to increase the amount of amide formation. For amine containing solvents, the presence of water and impurity amines is problematic considering the low solubility of the reactants. Addition of a lewis acid drying agent was found to be beneficial. An appreciable yield of H$_4$[MAC*] was obtained (2–3% macrocyclization yield, unoptimized) from the reaction (1 step) of TMDE bis oxazalone with DMP alkyl diamine in refluxing tripropylamine+CaO. Isolation of the product was by fractional recrystallization from toluene in combination with $^1$H NMR analysis.

The highest possible yield of H$_4$[MAC*] from alkyl diamine via the prior art method of Uffelman (4 steps from the alkyl diamine) is 8–10%. Clearly H$_4$[MAC*] can be obtained in appreciable yield via the oxazalone route.

Synthesis of Chelate Complexes

Figure 5:
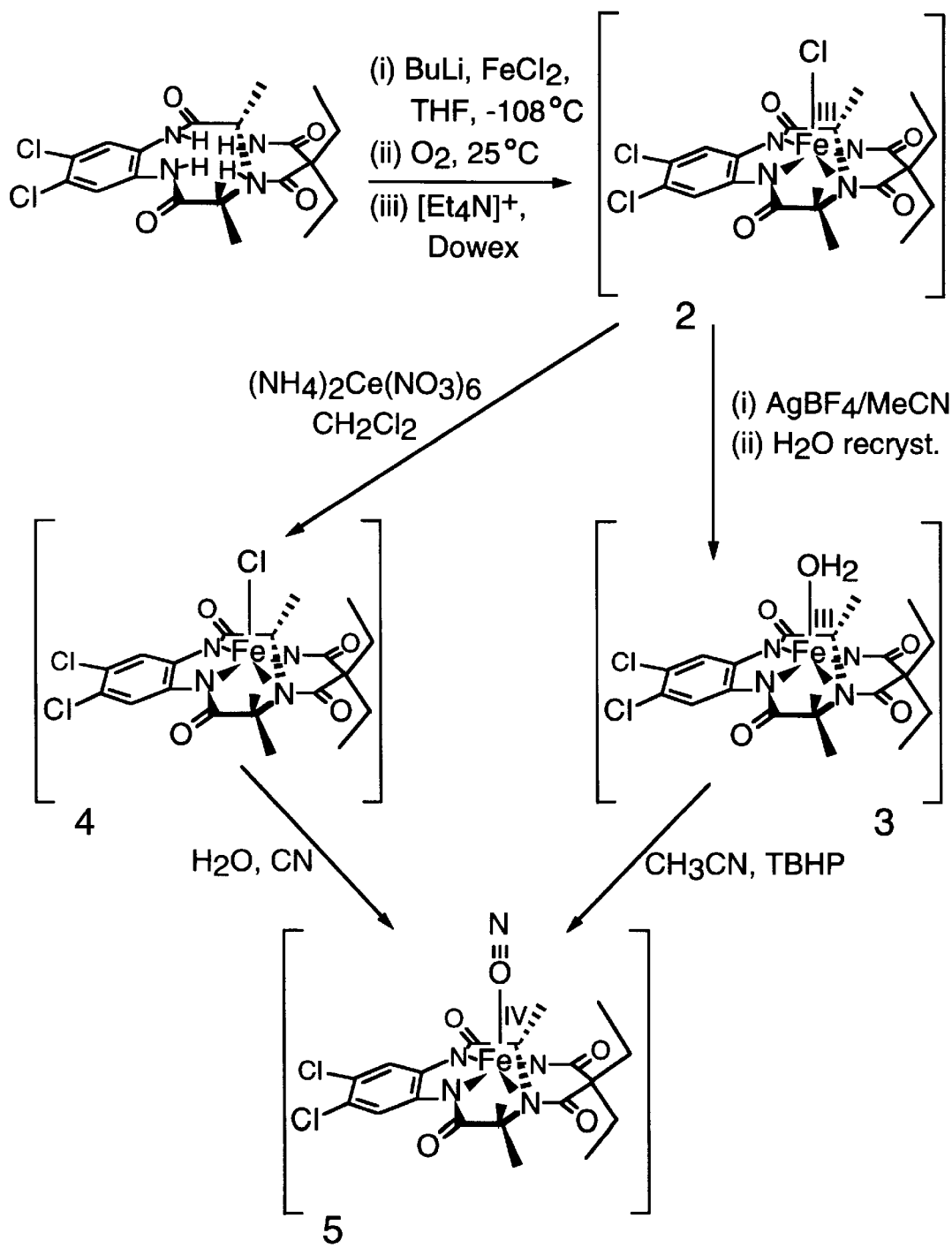
FIG. 5 is an illustration of several chelate complexes formed from the macrocyclic ligands synthesized by the method of the present invention.

The compounds labeled 2, 3, 4 and 5 in Examples 23–30 below are illustrated in FIG. 5.

Example 23

[Et$_4$N]2 and [Et$_4$N]3. [the tetraethylammonium salts of iron(III) chloro TMDE-DCB monoanion and iron(III) aquo TMDE-DCB monoanion respectively]. The parent macrocyclic tetraamide of any of Examples 10–18 or 21–22 above (525 mg, 1.1 mmol) is dissolved in tetrahydrofuran (40 mL, Aldrich) under N$_2$. Using schlenk techniques, tert-butyllithium (2.6 mL, 4.4 mmol, 1.7 M in 2,4-dimethylpentane, Aldrich) was added to the solution under N$_2$ at −108° C. Ferrous chloride (anhydrous, 155 mg, 1.2 mmol, Alfa) was then added and the solution warmed to room temperature with stirring (16 h), to yield an olive-green precipitate, an air sensitive Fe$^{II}$ complex. Air was admitted through a drying tube (2 h), and the orange solid was collected and washed with CH$_2$Cl$_2$ (2×10 mL). The resulting orange powder was dried under reduced pressure. Yield: 595 mg (≈93%). Because of variable salvation and limited solubility, the lithium salt was converted to the tetraethylammonium salt for further use. The lithium salt (595 mg) in CH$_3$OH (50 mL) was loaded on an ion exchange column (Dowex® 50×2-100, 25 g, 2 cm×12.5 cm) that had been presaturated with [Et$_4$N]$^+$ cations, and the orange band was eluted with CH$_3$OH (100 mL). The solvent was removed under reduced pressure. The residue was suspended in CH$_2$Cl$_2$ (20 mL) and the mixture was filtered. The solvent was removed from the mother liquor under reduced pressure giving an orange hygroscopic glassy residue of [Et$_4$N]2 that was used without further purification. IR (Nujol/NaCl, cm$^{-1}$): 1619 (ν(CO)amide), 1575 (ν(CO) amide), 1534 (ν(CO)amide). Careful purification of an iron (III) starting material was more conveniently approached by dealing with the axial aqua monoanionic complex rather than this axial chloro dianionic complex. [Et$_4$N]2 (550 mg, ca. 0.7 mmol) was dissolved in CH$_3$CN (50 mL). Silver tetrafluoroborate (140 mg, 0.7 mmol) was dissolved in CH$_3$CN (2 mL) and was added to the solution which was stirred (1 h). The AgCl precipitate was filtered off and the solvent removed under reduced pressure. The resulting [Et$_4$N]3 was further purified by elution through a silica gel column (8% MeOH in CH$_2$Cl$_2$). The solvent was removed under reduced pressure and the product was recrystallized from H$_2$O. Yield: 360 mg (≈77%, variable salvation with water was found in different microcrystalline samples). IR (Nujol/NaCl, cm$^{-1}$): 1590 (ν(CO)amide), 1565 (ν(CO) amide), 1535 (ν(CO)amide). Anal. Calcd for C$_{29}$H$_{46}$N$_5$FeO$_5$Cl$_2$. (H$_2$O): C, 50.52; H, 7.02; N, 10.16.: Cl, 10.28. Found: C, 50.24; H, 6.84; N, 9.82; Cl, 10.32. ESIMS (negative ion): m/z 522.2, [3-H$_2$O]$^{1-}$ (100%); m/z 269.7, [3-H$^+$]$^{2-}$ (18%).

Example 24

[Et$_4$N]4. [the tetraethylammonium salt of iron(IV) chloro TMDE-DCB monoanion]. [Et$_4$N]2 (500 mg, ca. 0.6 mmol) was dissolved in CH$_2$Cl$_2$ (30 mL). Ammonium cerium(IV) nitrate (10.3 g, 18.3 mmol) was added to the solution and the mixture was stirred (2 h). The solid cerium salts were removed by filtration. The purple product was obtained by removing the solvent under reduced pressure and drying under vacuum. Yield: 400 mg (≈95%). Purple crystals were obtained by recrystallization from CH$_2$Cl$_2$/Et$_2$O. IR (Nujol/NaCl, cm$^{-1}$): 1688 (ν(CO)amide), 1611 (ν(CO)amide), 1582 (ν(CO)amide). ESIMS (negative ion): m/z 557, [4]$^{-1}$ (100%); m/z 522, [4-Cl]$^{1-}$ (65%).

Example 25

Synthesis of [Ph$_4$P]5 [the tetraphenylphosphonium salt of iron(IV) cyano TMDE-DCB monoanion] from [Et$_4$N]4 [the tetraethylammonium salt of iron(IV) chloro TMDE-DCB monoanion] and NaCN.

[Et$_4$N]4 [the tetraethylammonium salt of iron(IV) chloro TMDE-DCB monoanion] (225 mg, 0.33 mmol) was suspended in H$_2$O (10 mL). Sodium cyanide (140 mg, 2.85 mmol) was dissolved in H$_2$O (10 mL) and added to the suspension and the mixture was sonicated (Branson 1200, 0.5 h). The purple suspension changed to a deep blue solution and nearly all the solid material dissolved. The mixture was filtered and the blue product was precipitated by adding PPh$_4$Cl [tetraphenylphosphonium chloride] dissolved in water (600 mg, 1.6 mmol, 10 mL, Aldrich). The blue precipitate was collected and washed with H$_2$O (2×10 mL). Yield: 250 mg (0.28 mmole, ≈85%). This material (120 mg) was further purified by thin layer chromatography (TLC) (Silica gel plate, GF, 20 cm×20 cm×1000 µm, 10:1 CH$_2$Cl$_2$:CH$_3$CN). The blue material was extracted from the silica gel with CH$_3$CN:CH$_2$Cl$_2$ (1:1, 60 mL). The solvent was removed under reduced pressure and the residue was dissolved in CH$_2$Cl$_2$ (3 mL) and filtered. Addition of pentane (150 mL) gave a blue powder (90 mg, 0.10 mmol) Yield on purification: 75%). IR (Nujol/NaCl, cm$^{-1}$): 2129 (v(CN)), 1659 (v(CO)amide), 1598 (v(CO)amide), 1571 (v(CO) amide). Anal. Calcd for: C$_{46}$H$_{44}$N$_5$FeOCl$_2$P: C, 62.18; H, 4.99; N, 7.88; Cl, 7.98. Found: C, 61.96; H, 5.04; N, 7.84; Cl, 8.06. ESIMS (negative ion): m/z 548.2, [5]$^{1-}$ (100%); m/z 522.1, [5-CN]$^{1-}$ (20%). For $^{13}$C-labeled cyanide: m/z 549.2, [5]$^{1-}$ (100%); m/z 522.1, [5-$^{13}$CN]$^{1-}$ (8%).

Example 26

The Synthesis of [Ph$_4$P]5 [the tetraphenylphosphonium salt of iron(IV) cyano TMDE-DCB monoanion] from Nitrile Cyanide Sources.

[Ph$_4$P]5 [the tetraphenylphosphonium salt of iron (IV) cyano TMDE-DCB monoanion] can be formed in the presence or absence of base. In the absence of base, the blue color fades to yellow-orange as the solvent is removed in the workup procedures. Therefore, product isolation to obtain the blue solid is best carried out in the presence of added base at a pH range of 9–10. The following reaction yields 5 with each of CH$_3$CN, CD$_3$CN, CH$_3$CH$_2$CN and (CH$_3$)$_2$CHCN as the solvent substrates. Base was not added to the catalytic reactions described. It was demonstrated that the blue compound is an effective catalyst precursor by adding isolated [Ph$_4$P]5 to an acetonitrile solution of TBHP (tertiary butyl hydroperoxide), both the solvent and oxidant were consumed indicating that although [Ph$_4$P]5 is formed as an end product of the catalytic oxidation process it is not a deactivated form of the catalyst.

Example 27

The Synthesis of [Ph$_4$P]5 in the Presence of Base.

[Et$_4$N]3 (160 mg, 0.23 mmol) was dissolved in the chosen nitrile solvent (6 mL), see Example 26. Tetraethylammonium hydroxide base was added (20 wt %, 0.370 mL, 0.52 mmol, Aldrich), then t-butyl hydroperoxide (90%, 0.605 mL, 5.4 mmol, Aldrich) was added dropwise with stirring (20 min) resulting in a blue solution. The remaining nitrile was removed under reduced pressure, leaving an oily blue residue which was dissolved in H$_2$O (15 mL) and filtered. The blue material was precipitated from the filtrate by addition of an aqueous solution of PPh$_4$Cl (800 mg, 2.1 mmol, Aldrich, 10 mL). The blue precipitate was collected and washed with H$_2$O (2×10 mL). Yield: 130 mg, 0.15 mmol (65%). Further purification was carried out as described in the [Ph$_4$P]5 section, Example 25.

Example 28

1-[2-((E)-2-butenyl-2-ethylamido)-2-methylpropanamido]-2-[5,5-dimethylhydantoin]-4,5-dichlorobenzene (i.e. a ligand decomposition product). [Et$_4$N]2 (130 mg, 0.13 mmol) was dissolved in CH$_3$CN (5 mL, Aldrich). A 90% solution of t-butyl hydroperoxide (0.445 mL, 4 mmol, Aldrich) was added slowly (3 min). The reaction mixture was stirred (25 min) and then all liquids were removed under reduced pressure. The blue residue was dissolved in CH$_2$Cl$_2$ and loaded onto a preparative thin layer chromatography (TLC) plate (Silica gel GF, 1000 µm, 20 cm×20 cm) and eluted with a 15% CH$_3$CN/85% CH$_2$Cl$_2$ solvent mixture. The product band was detected under UV irradiation at an Rf value of 0.3. Other product bands included blue [Et$_4$N]5, a brown-yellow species that remains at the origin, and two faint colorless bands present in less than 10% of the band found at 0.3 rf. The portion of the silica that contained the product was removed from the preparative plate and the product extracted with CH$_2$Cl$_2$:CH$_3$CN (1:1). The solution was filtered and the solvent was removed under reduced pressure. A solid was obtained by dissolving the residue in CH$_2$Cl$_2$ (3 mL) followed by addition of pentane (150 mL). This was collected by filtration and was washed with pentane (2×10 mL). Yield: 9 mg (14.8%). IR (Nujol/NaCl, cm$^{-1}$): 1780 (v(CO)hydantoin), 1723 (v(CO)hydantoin), 1665 (v(CO)amide), 1631 (v(CO)amide), 1582 (v(CO) amide). $^1$H NMR (CD$_3$CN, δ ppm): 0.83 (t, 3H, J=7 Hz), 1.4 (s, 6H), 1.45 (s, 6H), 1.70 (d, 3H, J=7 Hz), 2.25 (q, 2H, J=7 Hz) 6.25 (q, 1H, J=7 Hz), 6.60 (s, 1H, NH) 6.70 (s, 1H, NH) 7.48 (s, 1H, ArH), 8.10 (s, 1H, ArH), 9.10 (s, 1H, NH); $^1$H NMR (CD$_2$Cl$_2$, δ ppm): 0.97 (t, 3H, J=7 Hz), 1.27 (s, 12H) 1.75 (d, 3H, J=7 Hz) 2.30 (q, 2H, J=7 Hz) 5.50 (s, 1H, NH) 6.00 (s, 1H, NH), 6.27 (q, 1H, J=7 Hz) 7.35 (s, 1H, ArH), 8.30 (s, 1H, ArH), 9.77 (s, 1H, NH). $^{13}$C NMR (CD$_2$Cl$_2$, δ ppm): 13.4, 13.6, 20.2, 25.4, 30.0, 58.5, 59.6, 121.9, 125.2, 127.8, 129.7, 130.3, 133.8, 134.9, 139.2, 154.3, 170.5, 172.5, 175.9.

Example 29

X-ray Crystal Structure Data and Refinement for [Et$_4$N]3 H$_2$O.

C$_{29}$H$_{48}$Cl$_2$FeN$_5$O$_6$, M=689.47, Triclinic, Space group P-1, a=9.899(2); b=11.771(2); c=14.991(4) Å, α=95.33(2); β=100.09(2); γ=92.31(2)*, V=1709.6(6) Å$^3$, D$_{obs}$=1.33 g cm$^{-3}$, D$_{calcd}$ (Z=2)=1.339 g cm$^{-3}$, T=293 K, λ=0.71069 Å, µ=0.64 mm$^{-1}$, trans coeff. 0.87–1.00. Diffraction data were collected at room temperature on an Enraff-Nonius CAD-4 diffractometer using graphite monochromated Mo-Kα radiation. Three reflections were monitored throughout data collection, only random fluctuations in intensity being observed. The structure was solved by direct methods. Hydrogen atoms bonded to the carbon were included in calculated positions with C—H bond distance of 0.96 Å and were refined using a riding model with a thermal parameter 20% greater than the parent carbon. Hydrogen atoms of the water molecule were located from electron density difference maps and their coordinates allowed to refine with the thermal parameter fixed at 20% greater than that of the oxygen. Refinement was by full-matrix least squares on F$^2$ with scattering factors taken from the International Tables. All non-hydrogen atoms were refined with anisotropic thermal parameters. The final difference maps were featureless. Refinement converged to R=0.053, wR2=0.112 with weights 1.0/[σ$^2$(F$_o^2$)+{0.0652(F$_o^2$+2 F$_c^2$)/}$^2$] for 2262 observed reflections.

Example 30

X-ray Crystal Structure Data and Refinement for [Et$_4$N]4.

Single crystal's of [Et$_4$N]4 at 20±1° C. are monoclinic, space group P2$_1$/c-C$^5_{2h}$ (No. 14) with a=9.958(2) Å, b=14.956(3) Å, c=22.688(5) Å, α=90.00°, β=93.83(2)°, $\gamma=90.00°$, $V=3372(1)$ Å$^3$, and $Z=4$ ($d_{calcd}=1.357$ g cm$^{-3}$; $\mu_a(\text{CuK}\overline{\alpha})=6.17$ mm$^{-1}$). A total of 4626 independent absorption-corrected reflections having $2\theta(\text{CuK}\overline{\alpha})<115.0°$ were collected using $\theta$–$2\theta$ scans and Ni-filtered CuK$\overline{\alpha}$ radiation. The structure was solved using "Direct Methods" techniques with the Nicolet SHELXTL software package as modified at Crystalytics Company. The resulting structural parameters have been confined to a convergence of $R_1$(unweighted, based on F)=0.037 for 2680 independent reflections having $2\theta(\text{CuK}\overline{\alpha})<115.0°$ and $I>3\sigma(I)$. The ten methyl groups were refined as rigid rotors with sp$^3$-hybridized geometry and a C—H bond length of 0.96 Å. The initial orientation of each methyl group was determined from difference Fourier positions for the hydrogen atoms. The final orientation of each methyl group was determined by three rotational parameters. The refined positions for the rigid rotor methyl groups gave C—C—H angles which ranged from 103°–118°. The remaining hydrogen atoms were included in the structure factor calculations as idealized atoms (assuming sp$^2$- or sp$^3$-hybridization of the carbon atoms and a C—H bond length of 0.96 Å) riding on their respective carbon atoms. The isotropic thermal parameter of each hydrogen atom was fixed at 1.2 times the equivalent isotropic thermal parameter of the carbon to which it is covalently bonded.

What we claim is:

1. A method comprising:

reacting stoichiometric amounts or more of an amino carboxylic acid or a protected/activated for thereof with an activated dervative selected from the group consisting of oxalates and malonates in the presence of a solvent and heat to produce an amide intermediate having the structure

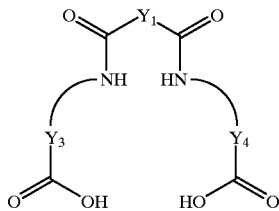

wherein $Y_1$ represents zero, one or two carbon containing nodes for substitution, and $Y_3$ and $Y_4$ each represent one or two carbon containing nodes for substitution, each said node containing a C(R) or a C(R)$_2$ unit and each R substituent is the same or different from the remaining R substituents and is selected from the group consisting of alkyl, aryl, hydrogen, halogen, CH$_2$CF$_3$, CF$_3$ and combinations thereof, or together with a paired R substituent bound to the same carbon atom form a cyclopentyl or cyclohexyl ring.

2. The method of claim 1 wherein the amino carboxylic acid is selected from the group consisting of $\alpha$ and $\beta$ amino acids.

3. The method recited in claim 1 wherein said amino carboxylic acid or said protected/activated form of an amino carboxylic acid has the formula

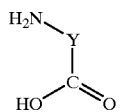

wherein Y is C(R$_3$)(R$_4$), C(R$_5$)(R$_6$)C(R$_7$)(R$_8$), or

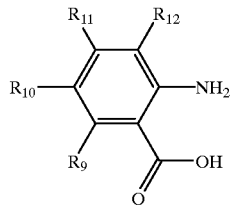

and R$_3$, R$_4$, R$_5$, R$_6$, R$_7$, R$_8$, R$_9$, R$_{10}$, R$_{11}$, and R$_{12}$ are the same or different, pairwise and cumulatively, and comprise hydrogen, ketones, aldehydes, carboxylic acids, hidden or protected/activated carboxylic acids, esters, ethers, oxazalones, anhydrides, acyl halides, nitriles, oxazalines, acyl oximes, amides, hidden or protected/activated amines, imines, imides, amides, azides, azo compounds, nitrilium ions, hydrazines, carbanates, enamines, n-oxides, isocyanates, isothiocyanates, nitro, sulfonyls, sulfates, phosphoryls, phosphates, phosphazos, silyl, siloxanes, alkyl, alkenyl, alkynyl, halo, aryl, CH$_2$CF$_3$, CF$_3$ and combinations thereof.

4. The method of claim 1 wherein the heat to form said and intermediate is at a temperature equal to or less than about 70° C.

5. The method of claim 1 wherein the amino carboxylic acid is an $\alpha$ spiro-cyclohexyl amino carboxylic acid and the solvent is added in multiple aliquots at periodic intervals to yield a bis-cyclohexyl intermediate and an oxazalone species.

6. The method of claim 5 further comprising the step of hydrolyzing the oxazalone species in the presence of solvent to the bis-cyclohexyl intermediate.

7. The method of claim 1 wherein the solvent is selected from the group consisting of solvents suitable for performing acylations and aprotic solvents.

8. The method of claim 1 wherein the malonate activated derivative is selected from the group consisting of unsubstituted, monosubstituted and disubstituted malonates.

9. The method of claim 1 wherein the malonate activated derivative has the structure

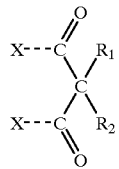

and the oxalate activated derivative has the structure

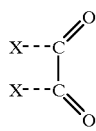

wherein X is hydroxy, halogen or protected/activated hydroxy and $R_1$ and $R_2$ are the same or different, and are comprised of substituents containing hydrogen, ketones, aldehydes, carboxylic acids, hidden or protected/activated carboxylic acids, esters, ethers, amines, hidden or protected/activated amines, imines, amides, nitro, sulphonyls, sulfates, phosphoryls, phosphates, silyl, siloxanes, alkyl, alkenyl, alkyl, halo, or aryl.

10. The method of claim 1 further comprising adding to the intermediate a diamine in the presence of solvent and a coupling agent, and heating the resulting mixture for a period of time sufficient to form macrocyclic tetraamido compounds.

11. The method of claim 10 wherein the diamine is added under anhydrous conditions.

12. The method of claim 10 wherein said diamine is selected from the group consisting of n,n+1 alkyl diamines and 1,2-aryl diamines, substituted n,n+2 alkyl diamines, substituted o-amino benzylamines and substituted 1,8-diamino napthalenes.

13. The method of claim 10 wherein the coupling agent is selected from the group consisting of a phosphorous halide compound and pivaloyl chloride.

14. The method of claim 10 wherein the diamines are selected from the group having the general structure

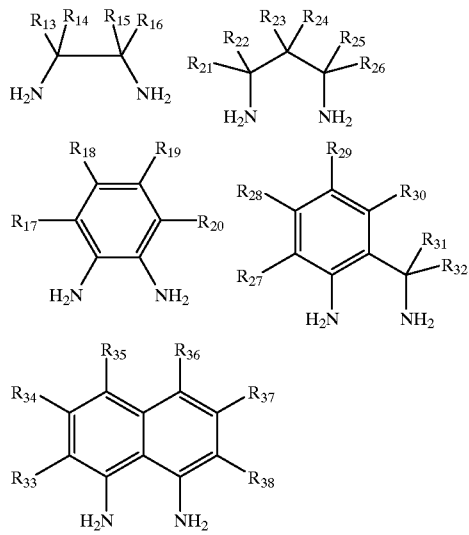

wherein $R_{13}$ to $R_{38}$ are the same or different, pairwise and cumulatively, and comprise hydrogen, $CF_3$, ketones, aldehydes, esters, ethers, amines, imines, arides, nitro, sulphonyls, sulfates, phosphoryls, phosphates, silyl, siloxanes, alkyl, heteroatom substituted alkyl, alkenyl, alkynyl, halo, aryl and protected/activated and hidden carboxylic acids and protected/activated and hidden amines.

15. The method of claim 14 wherein the R groups of $C(R_3)(R_4)$, $C(R_5)(R_6)$ or $C(R_6)(R_7)$ are fused together to form cyclopentyl or cyclohexyl rings.

16. The method of claim 10 further comprising complexing a transition metal to the N-donors of said macrocylic tetraamido compound.

17. The method of claim 16 wherein said transition metal is a group VIA, VIIA, VIII or IB transition metal.

18. The method of claim 16 wherein said complexing step further comprises:
  deprotonating the N-donors of the macrocyclic tetraamido compound by treatment with a base;
  adding a metal ion; and,
  oxidizing to produce a metal chelate complex having the structure:

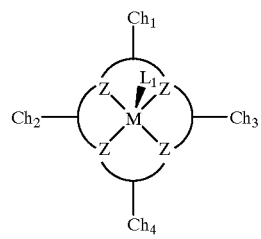

wherein M is the metal; Z is N; $L_1$ is a ligand; and, $Ch_1$, $Ch_2$, $Ch_3$ and $Ch_4$ are oxidation resistant components which are the same or different and which form five- to six-membered rings in combination with the adjacent ZMZ atoms.

19. The method recited in claim 18 wherein the ligand, $L_1$, is selected from the group consisting of halide ions, $CN^-$, $H_2O$, $OH^-$, ROH, $NH_3$, amines, carboxylate, phenoxide, pyridine, ether, sulfoxide, ketone, nitriles, isonitriles and carbonate.

20. The method recited in claim 18 wherein the oxidation step comprises exposure to air, oxygen, chlorine, bromine or benzoyl peroxide.

21. The method recited in claim 18 wherein the base is selected from the group consisting of lithium bis-trimethylsilamide, lithium diisopropyl amide, t-butyl lithium, n-buty lithium, phenyl lithium.

22. The method recited in claim 18 wherein the base is a noncoordiating organic soluble base.

23. The method of claim 18 further comprising combining the metal chelate complex with an oxygen atom transfer oxidant.

24. The method of claim 20 further comprising attaching a protecting group to the diamine before addition of the diamine to the intermediate.

25. The method of claim 4 further comprising
  (4) adding to the product of claim 24, THF, a base and a metal salt in the presence of oxygen to form a metal-lated amino pendant macrocyclic tetraamido compound in protected form; and
  (5) removing the protecting group.

26. The method of claim 25 further comprising covalently attaching the amino pendant macrocyclic tetraamido compound to a support.

27. The method of claim 26 wherein the support is selected from the group consisting of polymers, sand and molecules/substrates having functional groups which form a covalent bond with said amino.

28. The method of claim 26 wherein the amino pendant metallated macrocyclic compound is attached to the support by reacylation of the pendant amino group with acryloyl chloride; and
  copolymerizing with an excess of acryloyl monomers to yield an acrylic polymer having a plurality of macrocyclic metallated complexes as side chains.

* * * * *

UNITED STATES PATENT AND TRADEMARK OFFICE
CERTIFICATE OF CORRECTION

PATENT NO. : 6,011,152
DATED : January 4, 2000
INVENTOR(S) : Gordon-Wylie et al.

Page 1 of 2

It is certified that error appears in the above-identified patent and that said Letters Patent is hereby corrected as shown below:

Title page,
OTHER PUBLICATIONS,
Seventh reference, delete "Aromatuc" and substitute therefor -- Aromatic --;
Eighth reference, delete "Maganese" and substitute therefore --Manganese --;
Last reference, delete "Joh" and substitute therefor -- John --.

Column 8,
Line 36, delete "macrocylic" and substitute therefor -- macrocyclic --.

Column 24,
Line 21, delete "Kashdan." and substitute therefor -- Kashdan, --.

Columns 27/28, Table 4,
First column, the last line under the subsection entitled "Disubstituted malonates", delete dichloro malonic acid" and substitute therefor -- difluoro malonic acid --;
Second column, the tenth line under the section entitled "Monosubstituted malonates", after "4-methoxybenzal" insert -- malonate --.

Column 31, Table 5,
Line 15, first column, after "O,O'" insert -- - --;
Fourth column, the tenth line under the section entitled "Derivative of β-Amino Carboxylic Acids (6ac)", delete "sulfanoyl" and substitute therefor -- sulfamoyl --.

Column 37,
Line 14, delete "follows;" and substitute therefor -- follows. --.

Column 41,
Line 30, delete "Y," and substitute therefor -- $Y_1$ --.

Column 42,
Line 37, delete "thr" and substitute therefor -- the --.

Column 48,
Line 25, delete "Electrosptay" and substitute therefor -- Electrospray --.

Column 49,
Line 36, delete "mono nitroveratrole" and substitute therefor -- mononitroveratrole --.

UNITED STATES PATENT AND TRADEMARK OFFICE
CERTIFICATE OF CORRECTION

PATENT NO.   : 6,011,152
DATED        : January 4, 2000
INVENTOR(S)  : Gordon-Wylie et al.

It is certified that error appears in the above-identified patent and that said Letters Patent is hereby corrected as shown below:

Column 53,
Line 10, delete "9/2" and substitute therefor -- 9.2 --.

Column 62,
Line 61, delete "$F_c^2) /\}^2]$" and substitute therefor -- $Fc^2) /3\}^2]$ --.

Column 63,
Line 34, delete "for" and substitute therefor -- form --.

Column 64,
Line 36, delete "and" and substitute therefor -- amide --; and

Column 66,
Line 46, delete "4" and substitute therefor -- 24 --.

Signed and Sealed this

Fifteenth Day of January, 2002

Attest:

JAMES E. ROGAN
*Director of the United States Patent and Trademark Office*

*Attesting Officer*